US012692522B2

(12) United States Patent
Kwon et al.

(10) Patent No.: US 12,692,522 B2
(45) Date of Patent: ***Jul. 28, 2026

(54) MICROORGANISM HAVING ENHANCED L-THREONINE PRODUCING ABILITY AND METHOD FOR PRODUCING THREONINE USING THE SAME

(71) Applicant: CJ CHEILJEDANG CORPORATION, Seoul (KR)

(72) Inventors: Su Yon Kwon, Seoul (KR); Mina Baek, Seoul (KR); Seung-ju Son, Seoul (KR); Kwang Woo Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 633 days.

This patent is subject to a terminal disclaimer.

(21) Appl. No.: 17/600,594

(22) PCT Filed: Mar. 10, 2020

(86) PCT No.: PCT/KR2020/003318
§ 371 (c)(1),
(2) Date: Sep. 30, 2021

(87) PCT Pub. No.: WO2020/218737
PCT Pub. Date: Oct. 29, 2020

(65) Prior Publication Data
US 2022/0170059 A1 Jun. 2, 2022

(30) Foreign Application Priority Data
Apr. 22, 2019 (KR) ........................ 10-2019-0046935

(51) Int. Cl.
| *C12P 13/08* | (2006.01) |
| *C07K 14/34* | (2006.01) |
| *C12N 9/06* | (2006.01) |
| *C12N 9/10* | (2006.01) |
| *C12N 9/18* | (2006.01) |
| *C12N 15/77* | (2006.01) |

(52) U.S. Cl.
CPC .............. *C12P 13/08* (2013.01); *C07K 14/34* (2013.01); *C12N 9/0016* (2013.01); *C12N 9/1014* (2013.01); *C12N 9/1029* (2013.01); *C12N 9/18* (2013.01); *C12N 15/77* (2013.01); *C12Y 104/04002* (2013.01); *C12Y 203/01181* (2013.01); *C12Y 301/01013* (2013.01)

(58) Field of Classification Search
CPC ................................. C12N 15/77; C12P 13/08
See application file for complete search history.

(56) References Cited

U.S. PATENT DOCUMENTS

| 4,601,983 A | 7/1986 | Nakamori et al. |
| 9,896,704 B2 | 2/2018 | Hook et al. |
| 2017/0051324 A1 | 2/2017 | Ochrombel et al. |

FOREIGN PATENT DOCUMENTS

| KR | 10-0620092 B1 | 9/2006 |
| KR | 10-0924065 B1 | 10/2009 |
| KR | 10-1126041 B1 | 3/2012 |
| KR | 10-1335853 B1 | 12/2013 |
| KR | 20140102393 A | 8/2014 |
| KR | 10-1947959 B1 | 2/2019 |
| WO | WO 03/006666 A3 | 1/2003 |
| WO | WO 2006/065095 A1 | 6/2006 |
| WO | WO 2006/138689 A2 | 12/2006 |
| WO | WO 2009/096689 A1 | 8/2009 |

OTHER PUBLICATIONS

Corynebacteirum stationis. ATCC. Retrieved on Jun. 4, 2024.*
Fransceus. J Ind Microbiol Biotechnol. May 2017;44(4-5):687-695.*
Sanavia. Computational and Structural Biotechnology Journal, vol. 18, 2020, pp. 1968-1979.*
Studer. Residue mutations and their impact on protein structure and function: detecting beneficial and pathogenic changes. Biochem. J. (2013) 449, 581-594.*
NZ_CP014279.1 GenBank Database. Apr. 11, 2017.*
A0A2S8CFK7_9CORY. UniProtKB/TrEMBL. Jul. 18, 2018.*
Office Action of JP Application No. 2021-551564 dated Aug. 23, 2022; 5 pages.
Dong et al., "Metabolic engineering of *Escherichia coli* and Corynebacterturn giutamicum for the production of $_L$-threonine", Biotechnology Advances, 2011, 29, pp. 11-23.
GenBank, PQM73464.1, "D-seriner/D-alanine/glycine transporter [*Corytnebacterum* sp. J0108-1361]", Mar. 3, 2018.
International Search Report and Written Opinion of PCT/KR2020/003318 mailing date of Jun. 19, 2020, together with the English translation of the international search report (total of 6 pages).
NCBI Reference Sequence: WP 079005619.1 dated Mar. 11, 2017, "D-serine/D-alanine/glycine transporter [Corynebacterium stationis]".
Akhverdian et al., "Application of the bacteriophage Mu-driven system for the integration/amplification of target genes in the chromosomes of engineered Gram-negative bacteria-mini review", Appl Microbiol Biotechnol 2011, 91:857-871.
Bernard et al., "Assignment of Brevibacterium stationis (ZoBell and Upham 1944) Breed 1953 to the genus *Corynebacterium*, as *Corynebacterium stationis* comb. nov., and emended description of the genus *Corynebacterium* to include isolates that can alkalinize citrate", International Journal of Systematic and Evolutionary Microbiology (2010), 60, pp. 874-879; DOI 10.1099/ijs.0.012641-0.
Cronan, John E. "Assembly of Lipoic Acid on Its Cognate Enzymes: an Extraordinary and Essential Biosynthetic Pathway", Microbiology and Molecular Biology Reviews, Jun. 2016, vol. 80, No. 2, pp. 429-450.

(Continued)

*Primary Examiner* — Yong D Pak
(74) *Attorney, Agent, or Firm* — Squire Patton Boggs (US) LLP

(57) ABSTRACT

The present application relates to a microorganism having an enhanced L-threonine producing ability and a method for producing L-threonine using the same.

7 Claims, No Drawings

Specification includes a Sequence Listing.

(56) References Cited

OTHER PUBLICATIONS

Ghrist and Stauffer, "The *Escherichia coli* glycine transport system and its role in the regulation of the glycine cleavage enzyme system", Microbiology, 1995, vol. 141, pp. 133-140.

Han et al., "Molecular Cloning and Expression of s-(2-Aminoethyl)-L-Cysteine Resistant Aspartokinase Gene of Corynebacterium glutamicum", Biotechnology Letters, 1991, vol. 13, No. 10, pp. 721-726.

Kalinowski et al., "The complete Corynebacterium glutamicum ATCC 13032 genome sequence and its impact on the production of L-aspartate-derived amino acids and vitamins", Journal of Biotechnology, 2003, vol. 104, pp. 5-25.

Lee, Kwang-Ho, et al., "Systems metabolic engineering of *Escherichia coli* for L-threonine production", Molecular Systems Biology 2007, vol. 3; Article No. 149; doi: 10.1038/msb4100196; 8 pages.

Simic et al., "Identification of glyA (Encoding Serine Hydroxymethyltransferase) and Its Use Together with the Exporter ThrE to IncreaseL-Threonine Accumulation by *Corynebacterium glutamicum*", Applied and Environmental Microbiology, Jul. 2002, vol. 68, No. 7, pp. 3321-3327.

Uhlman and Peyman, "Antisense Oligonucleotides: A New Therapeutic Principle", Chemical Reviews, Jun. 1990, vol. 90, No. 4, pp. 543-584.

* cited by examiner

SEQUENCE LISTING

```
<160> NUMBER OF SEQ ID NOS: 42

<210> SEQ ID NO 1
<211> LENGTH: 421
<212> TYPE: PRT
<213> ORGANISM: Artificial Sequence
<220> FEATURE:
<223> OTHER INFORMATION: Synthetic: C.gl lysC variant

<400> SEQUENCE: 1

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
            35                  40                  45

Glu Leu Leu Glu Leu Ala Ala Ala Val Asn Pro Val Pro Pro Ala Arg
        50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
        130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
        210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ser Asp Gly Arg
```

-continued

```
305                310                315                320

Arg Ala Met Glu Ile Leu Lys Lys Leu Gln Val Gln Gly Asn Trp Thr
                325                330                335

Asn Val Leu Tyr Asp Asp Gln Val Gly Lys Val Ser Leu Val Gly Ala
            340                345                350

Gly Met Lys Ser His Pro Gly Val Thr Ala Glu Phe Met Glu Ala Leu
            355                360                365

Arg Asp Val Asn Val Asn Ile Glu Lys Ile Ser Thr Ser Glu Ile Arg
    370                375                380

Ile Ser Val Leu Ile Arg Glu Asp Asp Leu Asp Ala Ala Ala Arg Ala
385                390                395                400

Leu His Glu Gln Phe Gln Leu Gly Gly Glu Asp Glu Ala Val Val Tyr
                405                410                415

Ala Gly Thr Gly Arg
            420

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
tcgagctcgg tacccgctgc gcagtgttga atac                          34

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
tggaaatctt ttcgatgttc acgttgacat                               30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
atgtcaacgt gaacatcgaa aagatttcca                               30

<210> SEQ ID NO 5
<211> LENGTH: 34
<212> TYPE: DNA
<213> ORGANISM: Artificial Sequence
<220> FEATURE:
<223> OTHER INFORMATION: primer

<400> SEQUENCE: 5
ctctagagga tccccgttca cctcagagac gatt                          34

<210> SEQ ID NO 6
<211> LENGTH: 445
<212> TYPE: PRT
<213> ORGANISM: Artificial Sequence
<220> FEATURE:
<223> OTHER INFORMATION: Synthetic: C.gl Hom variant
```

-continued

```
<400> SEQUENCE: 6

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
            35                  40                  45

Gly Gly Pro Leu Glu Val Arg Gly Ile Ala Val Ser Asp Ile Ser Lys
        50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
    290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
            340                 345                 350

Ala Asn Leu Pro Ile Ala Asp Phe Gly Glu Thr Thr Thr Arg Tyr His
        355                 360                 365

Leu Asp Met Asp Val Glu Asp Arg Val Gly Val Leu Ala Glu Leu Ala
    370                 375                 380

Ser Leu Phe Ser Glu Gln Gly Ile Ser Leu Arg Thr Ile Gln Gln Glu
385                 390                 395                 400

Glu Arg Asp Asp Asp Ala Arg Leu Ile Val Val Thr His Ser Ala Leu
                405                 410                 415
```

Glu Ser Asp Leu Ser Arg Thr Val Glu Leu Leu Lys Ala Lys Pro Val
        420                 425                 430

Val Lys Ala Ile Asn Ser Val Ile Arg Leu Glu Arg Asp
        435                 440                 445

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
tcgagctcgg taccccaccg gcgctgacta tgc                                     33

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
cgcgctcttc ctgttggatt gtacgcaggg                                         30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ccctgcgtac aatccaacag gaagagcgcg                                         30

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
ctctagagga tcccgataga cagatttgtc cacg                                    34

<210> SEQ ID NO 11
<211> LENGTH: 1611
<212> TYPE: DNA
<213> ORGANISM: Corynebacterium glutamicum

<400> SEQUENCE: 11
atgcaccacg agcaacccga agggtgcgaa gtgggcattc gtagaacaat cccagaggaa       60
agccgtacgg ctttcctcga catgatcaat caaggtatgt caggtcttgc tgcgtctaca      120
gcggtcgggg tcagtgaatt caccgggcga aagtgggcga aggccgccgg ggtgaaactg      180
acccgcggcc cgcgaggtgg caatgctttt gacaccgccg agaaacttga gattgcagcc      240
agcatgctag agaaaggatg cctaccccga gaaatcggcg agtatgtcgg catgactcgg      300
gccaatatat ccctatggcg caaacaaggc ccagacaagc ttcgccaacg cgcagccacc      360
ttgcgcaccg gcaagcgagc agctgaattc atccacgccc cggtgatggg cccttattat      420
gggccacgca cactccatca agtgttgcgt gaggactaca acactgtt tgacgagtta      480

```
tctgcgttgg ggttgccagc acaggtgtgt ggggccttac ttcatcttgc tccaccacca      540
tcattacgct tttcttatat gtcgtgtgta gtgccgttat ttgctgatga aatcaaagtc      600
gtaggacaag gcacacgatt atcgttagaa gagaaaatga tgatccaacg tttccatgac      660
accggggtca gtgcagcaga aatcggtcga cgcctgggtc ggtgtcggca aacaatttcc      720
agggaacttc gacgtggtca agatgatgat ggacgttatc gtgcacgcga ctcctatgaa      780
ggtgcgatca ggaaactagc gcgtccgaaa acaccgaaac ttgatgccaa tcgtaggctt      840
cgggctgtgg tggtcgaggc gttgaataat aaattatctc cggagcagat ttctggtctt      900
ttagccaccg agcatgctaa cgatagctct atgcagatta gtcatgaaac tatttaccag      960
gcgttatatg ttcaaggtaa aggggcgttg cgtgatgaat tgaaggtgga gaaatttctt     1020
cgtaccggtc ggaagggacg taaaccgcag tcgaagttgc catcgagagg taagccgtgg     1080
gtggagggtg cgttgattag tcaacgccca gcagaagttg ctgatcgtgc tgtgcctggg     1140
cactgggagg gcgatttagt aattggtggt gaaaaccaag cgacagcgtt ggtgacgttg     1200
gtggagcgca cgagccggtt gacgttgatt aagcggttgg gggttaatca tgaggcgtcg     1260
actgtgacgg atgcgttggt ggagatgatg ggtgatttgc cgcaggcgtt gcgtcggagt     1320
ttgacgtggg atcagggtgt ggagatggca gagcatgcgc ggtttagcgt ggtgaccaag     1380
tgtccggtgt ttttctgtga tcctcattcg ccgtggcagc gtgggtcgaa tgagaatacg     1440
aatggattgg tcagggattt tttcccgaag ggcactaatt ttgctaaagt aagtgacgaa     1500
gaagttcagc gggcacagga tctgctgaat taccggccgc ggaaaatgca tggttttaaa     1560
agcgcgacgc aggtatatga aaaaatcgta gttggtgcat ccaccgattg a             1611
```

```
<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
tcgagctcgg taccctctgg tggtagttcg tag                                    33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
ctcgagcata ctagtatccc cgcaaagatc ggc                                    33

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
actagtatgc tcgagtacac gatctggacc aac                                    33

<210> SEQ ID NO 15
<211> LENGTH: 33
<212> TYPE: DNA
<213> ORGANISM: Artificial Sequence
```

<220> FEATURE:
<223> OTHER INFORMATION: primer

<400> SEQUENCE: 15
ctctagagga tccctcaagc tgcctcgcaa cta                                    33

<210> SEQ ID NO 16
<211> LENGTH: 476
<212> TYPE: PRT
<213> ORGANISM: Corynebacterium ammoniagenes

<400> SEQUENCE: 16

Met Ala Ser Tyr Asp Pro Gly His Ser Gln Val Lys Asn Thr Gly Val
1               5                   10                  15

Glu Leu Asp Ser His Val Glu Ser Asp His Leu Gln Arg Gly Leu Ser
                20                  25                  30

Asn Arg His Ile Gln Leu Ile Ala Ile Gly Gly Ala Ile Gly Thr Gly
            35                  40                  45

Leu Phe Met Gly Ser Gly Lys Thr Ile Ser Leu Ala Gly Pro Ser Val
        50                  55                  60

Ile Leu Val Tyr Gly Ile Ile Gly Phe Met Leu Phe Phe Val Met Arg
65                  70                  75                  80

Ala Met Gly Glu Leu Leu Leu Ser Asn Leu Asn Tyr Lys Ser Leu Arg
                85                  90                  95

Asp Ala Val Ser Asp Ile Leu Gly Pro Thr Ala Gly Phe Val Cys Gly
            100                 105                 110

Trp Thr Tyr Trp Phe Cys Trp Ile Val Thr Gly Met Ala Asp Val Val
        115                 120                 125

Ala Ile Thr Gly Tyr Thr Gln Tyr Trp Trp Pro Asp Ile Ala Leu Trp
        130                 135                 140

Ile Pro Gly Ala Leu Thr Ile Leu Leu Leu Gly Leu Asn Leu Val
145                 150                 155                 160

Ala Val Arg Leu Phe Gly Glu Leu Glu Phe Trp Phe Ala Ile Ile Lys
                165                 170                 175

Leu Val Ala Ile Thr Ala Leu Ile Leu Val Gly Ala Val Met Val Ile
                180                 185                 190

Ser Arg Phe Gln Ser Pro Asp Gly Asp Ile Ala Ala Val Ser Asn Leu
            195                 200                 205

Ile Asp His Gly Gly Phe Phe Pro Asn Gly Ile Thr Gly Phe Leu Ala
        210                 215                 220

Gly Phe Gln Ile Ala Ile Phe Ala Phe Val Gly Val Glu Leu Ala Gly
225                 230                 235                 240

Thr Ala Ala Ala Glu Thr Lys Asp Pro Glu Lys Asn Leu Pro Arg Ala
                245                 250                 255

Ile Asn Ser Ile Pro Ile Arg Ile Val Val Phe Tyr Ile Leu Ala Leu
            260                 265                 270

Ala Val Ile Met Met Val Thr Pro Trp Asp Lys Val His Ser Asp Ser
        275                 280                 285

Ser Pro Phe Val Gln Met Phe Ala Leu Ala Gly Leu Pro Ala Ala Ala
        290                 295                 300

Gly Ile Ile Asn Phe Val Val Leu Thr Ser Ala Ala Ser Ser Ala Asn
305                 310                 315                 320

Ser Gly Ile Phe Ser Thr Ser Arg Met Leu Phe Gly Leu Ala Arg Glu
                325                 330                 335

Gly Gln Ala Pro Lys Arg Trp Gly Ile Leu Ser Arg Asn Gln Val Pro

-continued

```
             340              345              350
Ala Arg Gly Leu Leu Phe Ser Val Ala Cys Leu Val Pro Ser Leu Ala
        355              360              365

Ile Leu Tyr Ala Gly Ala Ser Val Ile Asp Ala Phe Thr Leu Ile Thr
    370              375              380

Thr Val Ser Ser Val Leu Phe Met Val Val Trp Ser Leu Ile Leu Ala
385              390              395              400

Ala Tyr Leu Val Phe Arg Arg Lys Phe Pro Glu Arg His Ala Ala Ser
            405              410              415

Lys Phe Lys Val Pro Gly Gly Ala Phe Met Cys Trp Val Val Leu Ala
            420              425              430

Phe Phe Ala Phe Met Val Val Val Leu Thr Phe Glu Asn Asp Thr Arg
        435              440              445

Ser Ala Leu Met Val Thr Pro Ile Trp Phe Val Ile Leu Leu Ala Gly
    450              455              460

Trp Phe Ile Ser Gly Gly Val Lys Arg Ala Arg Lys
465              470              475
```

```
<210> SEQ ID NO 17
<211> LENGTH: 1431
<212> TYPE: DNA
<213> ORGANISM: Corynebacterium ammoniagenes

<400> SEQUENCE: 17
atggcatctt atgatcccgg gcattcacag gttaaaaata caggagtaga actcgactct        60
cacgtggagt cagaccatct ccaacgcggt cttagcaacc acatatccca gttgattgcc       120
attggcggtg ctatcggcac cggactattt atgggatcgg gcaaaaccat ctcccttgct       180
ggtccttccg taatcttggt gtatggcatc atcggtttta tgctcttctt cgtcatgcgg       240
gcgatgggtg agcttttgct ctcgaacctc aactacaagt cattgcgtga tgccgtctcg       300
gacatcctcg ggctaccgc tggtttcgta tgcggctgga cctactggtt ctgctggatt       360
gtcacaggca tggctgatgt cgtggctatt accggctaca cccaatactg tggccagat       420 atcgcgctgt ggatacctgg agcattgacg attttattac tgctcgggtt aaatctcgtg       480
gcagtccgcc tctttggtga gttggaattt tggttcgcaa tcatcaagct ggtggctatt       540
actgcgctca tcctcgtcgg cgcggtgatg gttatttcgc gcttccaatc cccagacggc       600
gacattgcgg ctgtttccaa cctgatcgac catggcggct tcttcccgaa cggaatcacg       660
ggcttcctcg ccggattcca gattgctatc ttcgccttcg tcggcgtgga gcttgccggt       720
accgcggctg cagaaaccaa agacccagaa aagaatcttc ctcgcgcgat taactcgatt       780
cctattcgta tcgtcgtgtt ctacatcctg gctcttgcgg tcatcatgat ggttaccccca       840 tgggacaagg tccacagtga ctccagccca tttgtgcaga tgtttgccct ggctggactg       900
ccggcggcag caggcattat taacttcgtg gtgctgacat ctgctgcttc atccgcgaac       960
agtggtattt tctccacatc acgcatgctg ttcggtctgg ctcgcgaagg ccaagcgccc      1020
aagcgttggg gcatcttgtc ccgtaaccaa gtcccagccc gcggcctgct gttctcagta      1080
gcgtgcctgg tcccgagcct ggcaatcttg tacgccggcg ccagcgtcat tgacgccttt      1140
acgttgatta ccaccgtgtc ttctgtgctg ttcatggtgg tatggagcct gatcctcgcg      1200
gcgtaccttg tcttccgccg caagttccca gaacgccatg cagcatccaa gttcaaggtc      1260
ccaggcgggg cgtttatgtg ctgggttgtt ctcgctttct tcgcgtttat ggtcgttgta      1320
ctgacctttg aaaatgacac tcggtccgct ttgatggtca ccccaatctg gttcgtgatc      1380
```
ctcttggccg gctggttcat ctccggcgga gtcaagcgcg ctaggaagtg a          1431

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
cgaaaggaaa cactcatggc atcttatgat ccc                              33

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
gggttgggtt ttcccgatct cgagcgattg cgtggcctcc aac                   43

<210> SEQ ID NO 20
<211> LENGTH: 318
<212> TYPE: DNA
<213> ORGANISM: Artificial Sequence
<220> FEATURE:
<223> OTHER INFORMATION: Synthetic: cj7

<400> SEQUENCE: 20
agaaacatcc cagcgctact aatagggagc gttgaccttc cttccacgga ccggtaatcg   60
gagtgcctaa aaccgcatgc ggcttaggct ccaagatagg ttctgcgcgg ccgggtaatg  120
catcttcttt agcaacaagt tgaggggtag gtgcaaataa gaacgacata gaaatcgtct  180
cctttctgtt tttaatcaac atacaccacc acctaaaaat tccccgacca gcaagttcac  240
agtattcggg cacaatatcg ttgccaaaat attgtttcgg aatatcatgg gatacgtacc  300
caacgaaagg aaacactc                                               318

<210> SEQ ID NO 21
<211> LENGTH: 51
<212> TYPE: DNA
<213> ORGANISM: Artificial Sequence
<220> FEATURE:
<223> OTHER INFORMATION: primer

<400> SEQUENCE: 21
gccgatcttt gcggggatac tagtatgctc gagagaaaca tcccagcgct a          51

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
gagtgtttcc tttcgttg                                               18

<210> SEQ ID NO 23
<211> LENGTH: 470
<212> TYPE: PRT
<213> ORGANISM: Escherichia coli -continued

```
<400> SEQUENCE: 23

Met Val Asp Gln Val Lys Val Val Ala Asp Asp Gln Ala Pro Ala Glu
1               5                   10                  15

Gln Ser Leu Arg Arg Asn Leu Thr Asn Arg His Ile Gln Leu Ile Ala
            20                  25                  30

Ile Gly Gly Ala Ile Gly Thr Gly Leu Phe Met Gly Ser Gly Lys Thr
        35                  40                  45

Ile Ser Leu Ala Gly Pro Ser Ile Ile Phe Val Tyr Met Ile Ile Gly
    50                  55                  60

Phe Met Leu Phe Phe Val Met Arg Ala Met Gly Glu Leu Leu Leu Ser
65                  70                  75                  80

Asn Leu Glu Tyr Lys Ser Phe Ser Asp Phe Ala Ser Asp Leu Leu Gly
            85                  90                  95

Pro Trp Ala Gly Tyr Phe Thr Gly Trp Thr Tyr Trp Phe Cys Trp Val
            100                 105                 110

Val Thr Gly Met Ala Asp Val Val Ala Ile Thr Ala Tyr Ala Gln Phe
            115                 120                 125

Trp Phe Pro Asp Leu Ser Asp Trp Val Ala Ser Leu Ala Val Ile Val
    130                 135                 140

Leu Leu Leu Thr Leu Asn Leu Ala Thr Val Lys Met Phe Gly Glu Met
145                 150                 155                 160

Glu Phe Trp Phe Ala Met Ile Lys Ile Val Ala Ile Val Ser Leu Ile
            165                 170                 175

Val Val Gly Leu Val Met Val Ala Met His Phe Gln Ser Pro Thr Gly
            180                 185                 190

Val Glu Ala Ser Phe Ala His Leu Trp Asn Asp Gly Gly Trp Phe Pro
            195                 200                 205

Lys Gly Leu Ser Gly Phe Phe Ala Gly Phe Gln Ile Ala Val Phe Ala
    210                 215                 220

Phe Val Gly Ile Glu Leu Val Gly Thr Thr Ala Ala Glu Thr Lys Asp
225                 230                 235                 240

Pro Glu Lys Ser Leu Pro Arg Ala Ile Asn Ser Ile Pro Ile Arg Ile
            245                 250                 255

Ile Met Phe Tyr Val Phe Ala Leu Ile Val Ile Met Ser Val Thr Pro
            260                 265                 270

Trp Ser Ser Val Val Pro Glu Lys Ser Pro Phe Val Glu Leu Phe Val
    275                 280                 285

Leu Val Gly Leu Pro Ala Ala Ala Ser Val Ile Asn Phe Val Val Leu
    290                 295                 300

Thr Ser Ala Ala Ser Ser Ala Asn Ser Gly Val Phe Ser Thr Ser Arg
305                 310                 315                 320

Met Leu Phe Gly Leu Ala Gln Glu Gly Val Ala Pro Lys Ala Phe Ala
            325                 330                 335

Lys Leu Ser Lys Arg Ala Val Pro Ala Lys Gly Leu Thr Phe Ser Cys
            340                 345                 350

Ile Cys Leu Leu Gly Gly Val Val Met Leu Tyr Val Asn Pro Ser Val
            355                 360                 365

Ile Gly Ala Phe Thr Met Ile Thr Thr Val Ser Ala Ile Leu Phe Met
    370                 375                 380

Phe Val Trp Thr Ile Ile Leu Cys Ser Tyr Leu Val Tyr Arg Lys Gln
385                 390                 395                 400

Arg Pro His Leu His Glu Lys Ser Ile Tyr Lys Met Pro Leu Gly Lys
            405                 410                 415
```

-continued

```
Leu Met Cys Trp Val Cys Met Ala Phe Phe Val Phe Val Val Val Leu
            420                 425                 430

Leu Thr Leu Glu Asp Asp Thr Arg Gln Ala Leu Leu Val Thr Pro Leu
            435                 440                 445

Trp Phe Ile Ala Leu Gly Leu Gly Trp Leu Phe Ile Gly Lys Lys Arg
        450                 455                 460

Ala Ala Glu Leu Arg Lys
465                 470

<210> SEQ ID NO 24
<211> LENGTH: 1413
<212> TYPE: DNA
<213> ORGANISM: Escherichia coli

<400> SEQUENCE: 24
atggtagatc aggtaaaagt cgttgccgat gatcaggctc cggctgaaca gtcgctacgg     60
cgcaatctca caaaccgaca tattcagctt attgccattg gcggtgccat tggtacgggg    120
ttgtttatgg ggtctggcaa aacgattagc cttgccgggc cgtcgatcat tttcgtttat    180
atgatcattg gttttatgct cttttttcgtg atgcgggcaa tggggggaatt gctgctttcg    240 aatctggaat acaaatcttt tagtgacttc gcttccgatt tactcgggcc gtgggcagga    300
tatttcaccg gctggactta ctggttctgc tgggttgtaa ccggtatggc agacgtggtg    360
gcgatcacgg cttatgctca gttctggttc cccgatctct ccgactgggt cgcctcgctg    420
gcggtgatag tgctgctgct gacgctcaat ctcgccaccg tgaaaatgtt cggtgagatg    480
gagttctggt ttgcgatgat caaaatcgtc gccattgtgt cgctgattgt cgtcggcctg    540
gtcatggtgg cgatgcactt tcagtcaccg actggtgtgg aagcgtcatt cgcgcatttg    600
tggaatgacg gcggctggtt cccgaaaggt ttaagtggct tctttgccgg attccagata    660
gcggttttcg ctttcgtggg gattgagctg gtaggtacaa cagctgcgga aaccaaagat    720
ccagagaaat cactgccacg cgcgattaac tccattccga tccgtatcat tatgttctac    780
gtcttcgcgc tgattgtgat tatgtccgtg acgccgtgga gttcggtagt cccggagaaa    840
agcccgtttg ttgaactgtt cgtgttggta gggctgcctg ctgccgcaag cgtgatcaac    900
tttgtggtgc tgacctctgc ggcgtcttcc gctaacagcg gcgtcttctc taccagccgt    960
atgctgtttg gtctggcgca ggaaggtgtg gcaccgaaag cgttcgctaa actttctaag   1020
cgcgcagtac ccgcgaaagg gctgacgttc tcgtgtatct gtctgctcgg cggcgtggtg   1080
atgttgtatg tgaatcctag tgtgattggc gcgttcacga tgattacaac cgtttccgcg   1140
attctgttta tgttcgtctg gacgattatc ctttgctcgt accttgtgta tcgcaaacag   1200
cgtcctcatc tacatgagaa gtcgatctac aagatgccgc tcggcaagct gatgtgctgg   1260
gtatgtatgg cgttctttgt gttcgtggtc gtgttgctga cactggaaga tgacactcgc   1320
caggcgctgc tggttacccc gctgtggttt atcgcgctgg ggttgggctg ctgtttatt   1380 ggtaagaagc gggctgctga actgcggaaa taa                                 1413

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
```

```
cgaaaggaaa cactcatggt agatcaggta aaag                                34

<210> SEQ ID NO 26
<211> LENGTH: 43
<212> TYPE: DNA
<213> ORGANISM: Artificial Sequence
<220> FEATURE:
<223> OTHER INFORMATION: primer

<400> SEQUENCE: 26
gggttgggtt ttcccgatct cgagctgatg gatcacatca gtc                      43

<210> SEQ ID NO 27
<211> LENGTH: 2859
<212> TYPE: DNA
<213> ORGANISM: Corynebacterium ammoniagenes

<400> SEQUENCE: 27
atggatttca ttgcccgcca ccttgggcca gatgccacag aatctaagga catgctggcg     60
cgtgtgggtt atgacagcgt agaagcgctt gtcacctcag caatccccca gtccattagc    120
atcacggatg cgcttaatat gccgcaggca ttgagtgaga ccgacgcaca agccaagctt    180
cgcgcttacg ctgataaaaa tgtcgtgctg aagtctttct acggccaggg ctactcagac    240
accatcaccc ctgctgttat tcgccgcggt ttggtagaag acgctggttg gtacaccgct    300
tataccccat accagccaga aatttcccag ggtcgccttg agtcgctgct gaacttccag    360
accatggttc aagacctcac cggcttgcct attgcgaatg cttctttgct ggatgaggca    420
tcggcagttg ctgaggccgt gggtttgatg tctcgtgcgg tcaagaaggg ccgccgcgta    480
ctgctcgacg cccgtttgca cccacaggtt ctcaccgtgg cggcggagcg tgcccgagca    540
attgacctcg aagttgagat tgctgacttg agcaacggcg tggttggcga agacctcgtc    600
ggcgcagtag ttgcctacac cggtacggag ggcgatattt ttgacccacg tgctgttatc    660
gaagaaatcc atggccgcgg cggacttgtt tccgtcgcgg ctgacttgtt gtccttgctg    720
cttctggaag gcccaggctc gttcggtgca gacattgtca ttggttcctc ccaacgcttt    780
ggtgtgccgc tcttctttgg tggcccacac gctgctttca tggcagtaac tgacaagcta    840
aagcgtcaga tgccaggccg tttggtcggc gtatcggtcg attctgaggg ccgtcctgct    900
taccgcttgg cgctgcagac tcgtgaacag cacatccgcc gtgaacgcgc gacgtcaaat    960
atttgtaccg cgcaggcact tctggccaac gtggctgcca tgtacgccgt ctaccacggt   1020
ccagaaggct tgaaggagat tgctaaccac gtgcactcct tggctgcttc ctttgccggt   1080
gcagttacta ctcagggtct gaagattact tcctcggagt tcttcgacac cgttaccgtt   1140
gccggcgttg atgccgcatc cattaagttc agcttggaaa aggccggata cctggtcgcc   1200
accattggcg aggataaggt ttctgtctcc ttcggtgagt ccgcaaccca aggcgatgtt   1260
actgtcttgg cggacgcctt tggtgccgct gcagtagata tgcagatttc cccactgcct   1320
gaagcactca cccgcaccac cgaggtgctc acccacgaaa tctttaactc cattcactcc   1380
gaaacccaga tgatgcgtta cctgcgcaag ctcggtgata aggatctggc tctagatcgc   1440
accatgattc ctttgggctc atgcaccatg aagctcaacc caaccgcagc catggaaccg   1500
atcacctggc cagaattcgc caatgttcac ccttactccc ctgaatacgc aacccagggc   1560
tggcgtgagc tcattgaaga gttggaaggc tggttggctg agctgaccgg ctacgccaag   1620
gtttctatcc aaccaaacgc tggttcccag ggcgagctag ctggtctttt ggctatccgc   1680
cgctaccacg tcgcaaatgg tgacaccaac cgcgatatcg tgttgattcc tgcgtccgcg   1740
```

-continued

```
cacggcacca acgctgcctc cgcgaccctg gcaaatctgc gcgttgttgt ggttaagacc    1800
gccgaagacg gctccatcga tctggaagat ctcgatgcga agatcgccaa gcatggtcag    1860
aacatggccg gaatcatgat cacctaccca tccactcacg gcgtctttga cccagaggtt    1920
cgtgaagtct gcgacaagat ccatgccgct ggcggccagg tctacattga tggcgcaaac    1980
atgaatgctt tgactggttg ggctcagccg ggcaagttcg gtggcgatgt ctcgcacttg    2040
aacctgcaca agactttcac cattccgcac ggcggtggcg gcccaggtgt tggaccaatt    2100
ggtgtcgctg agcacctcat tccattcctg ccaacggatg ctgcagctga tgagctggat    2160
cctgctaacc caaccccagt agaacagggc gttccaatta ctgcttcgca gtttggttcc    2220
gctggtgttc tgccgattac ctgggcatac atcgcaatga ccggtggcga gggtctaacc    2280
tccgctactg cacacgccat cttgggtgct aactaccttg cgcgcgaact ctccgattcc    2340
ttcccaattc tgttcaccgg taatgaaggt cttgttgcgc acgagtgcat tttggatctg    2400
cgcgcgctaa ccgatgcctc aggcgttact gcagcagacg ttgccaagcg tttgatcgac    2460
tttggcttcc acgctcctac cctcgcattc ccagtggctg gcaccttgat ggtggaacct    2520
actgagtctg aggatattgc tgaactggat cgtttcattg aagcaatgcg caccatccgt    2580
gcggagattc aggaaatcat cgatggcaag atcgcatatg aagattcggt catccgccac    2640
gcaccttaca ccgcaccgtc agtctcaagc gatgattggg agtactcctt tagccgtgaa    2700
aaggccgcat ggccagttcc ttcactgcgt ttgaacaagt acttcccacc ggtacgccgc    2760
ctggatgaag cttacggcga ccgcaacctg gtgtgctcct gcccaccgcc agaggcattc    2820
gacttcgatg ccgacaccga ttccaccgag gaggcttaa                          2859
```

<210> SEQ ID NO 28
<211> LENGTH: 1104
<212> TYPE: DNA
<213> ORGANISM: Corynebacterium ammoniagenes

<400> SEQUENCE: 28

```
atgtcagaac tacgccagtc cccactgcac gcagagcacg aaaagctcgg cgcatccttt      60
accgcttttg gcccttggaa tatgccacta aagtacggca aggagctcga tgagcaccac     120
gcagtgcgta atgcagtcgg catgtttgac ctctcgcaca tgggtgagat ttgggtcaac     180
ggcccagacg ccgctgcatt tttgtcctat gcgctgatct ccaacatgga gaccgtgaaa     240
aatggcaagg cgaagtactc catgattgtt gctgaagacg gcggcatcat cgatgaccta     300
atttcctacc gtttctccga taccaagttc ttggtagtgc caaacgctgg caacactgat     360
gtggtttggg aagcttttaa tcagcgcatt gaaggcttcg atgtagaact caacaatgag     420
tccttggatg ttgcgatgat tgccctgcag ggccccaatg ctgccaaggt tctagttgaa     480
caggttgctg aagagtccaa ggaagaagta gaaaaccttc cttactatgc cgcaaccatg     540
gccaaagtcg cagacgttga caccatcgtc gcgcgcaccg gctacaccgg cgaagacggc     600
ttcgagctga tgatctacaa cgccgatgcg accaagctct ggcagctttt catcgaccaa     660
gatggtgtta ctccatgcgg tttagcttca cgcgattcct tgcgcttgga agctggcatg     720
cctttgtacg gcaatgagct ttcccgcgat atcacccctg tcgaggcagg catgggtgtg     780
gcgtttaaga gaagaccgc tgacttcgtc ggcgccgagg tcctgcgtca acgcttggaa     840
gaaggcccta agcaagttat caaggctttg acctcctctg agcgccgtgc agcgcgcacc     900
ggtgctgaaa tctatgccgg cgagcagttg gtaggcaccg taacttcggg tcagccatcg     960
```

-continued

```
ccgacgctgg gacaccctat tgccctggca ctggtagata ctgcagcaaa cctcgaagaa    1020
ggcgcagaag tagaagtgga tattcgcggc aagcgttacc ccttcaccgt taccaagacg    1080
cctttctata gccgcgagaa gtaa                                          1104

<210> SEQ ID NO 29
<211> LENGTH: 390
<212> TYPE: DNA
<213> ORGANISM: Corynebacterium ammoniagenes

<400> SEQUENCE: 29
atggctaacc tacctgcaga atttacttac tccgaagacc acgagtggat taacgccgct     60
caggacgcaa tcgttggcaa aactgttcgc atcggcatca cttctgttgc cgcagaccgt    120
cttggtgagg ttgtcttcgc tgagcttcca gcagttggcg atagcgtcac tgcaggtgaa    180
acctgtggtg aggttgaatc caccaagtcc gtttctgacc tgtacagccc tgtcaccggt    240
accgtgaccg ctgtgaacga gacagtgcac gatgattatg aaatcatcaa caatgatcct    300
ttcggtgaag gttggctgtt tgaggtcgag gttgaagaac tcggcgaggt tatgaccgct    360
gatgaatacg cggcagaaaa cggcatctaa                                    390

<210> SEQ ID NO 30
<211> LENGTH: 1062
<212> TYPE: DNA
<213> ORGANISM: Corynebacterium ammoniagenes

<400> SEQUENCE: 30
atgctccgca ttgaaaagaa gaatgcggag tcacccattg agcagaagcc gaggtggatc     60
cgcaaccagg tccgcactgg ccctggttat gaggacatga aaaagcgtgt tgctggcgct    120
ggcctgcaca ctgtctgcca ggaggcaggc tgtcctaata tccacgaatg ctgggagtcc    180
cgagaagcca ccttccttat cggcggtgac cgttgtactc gccgttgtga cttctgcgat    240
attgccactg gtaagccgca ggcattggac accgatgagc cgcgtcgcgt ttcggaaaac    300
atccaagaga tgaatctgaa ctacgccacg atcactggtg ttacccgtga tgaccttcca    360
gatgagggcg catggctata tgctgaagtg gttcgtaaga tccacgagaa gaaccctcac    420
acgggtgtag aaaacctcac cccggacttc tccggcaagc cagacctgct gcaggaagtc    480
ttcgaggctc gccctgaggt tttcgctcac aacttggaaa ccgttcctcg tattttcaag    540
cgtatccgcc cggcattccg ttatgagcgt tctctggatg ttttgcagca ggcacacgac    600
ttcggcctga tcaccaagtc gaacttgatc ttgggcatgg gtgaaactga ggaagagatt    660
caggaagctc tacgcgatat cgctctgtgt ggcactgaca tcattaccat tacgcagtac    720
ctgcgtcctg tcctcgtttt ccacccaatt gagcgttggg ttcgccctga ggagttcatt    780
gcgcactccg agtacgccaa ggaattgggc tttaccgtta tgtctggtcc tttggttcgt    840
tcttcttacc gcgcgggcaa gctctacacc caggcgatga aggcacgtgg ctgggagctg    900
ccagaaaatc tcaagcacct ggaagaaact tctgatggcg caaccgctca ggaagcttcg    960
tcgctgttga agaagtacgg cccttccgag gaaacgccag ttacttcccg catggcaaag   1020
acgcctgtgg gtgcagataa atttactgct agcatccgct aa                      1062

<210> SEQ ID NO 31
<211> LENGTH: 822
<212> TYPE: DNA
<213> ORGANISM: Corynebacterium ammoniagenes

<400> SEQUENCE: 31
```

```
atgactgctc cgcgtgaccc gttttttcccc gctgatcgtt ctattcgcgc ttctactgcc       60
ccggtagagg tgagacgttt aggtcgtatg gattatcaag aagcctggga ctatcaagca      120
gaagtcgcag cgcagcgcgc acgtgacgaa gttgcagaca cgttgctggt cgttgagcac      180
cccgctgtgt atacggcggg caagcgcacg cagcccgaag atatgcccac caacggtctt      240
ccggttatca atgttgatcg tggcggccgg attacctggc acggcgaggg ccagttggtg      300
gtctacccga ttatcaagtt ggcagagcct gtcgatgtcg tcgattatgt ccgccgtctg      360
gaagaagctg ttattcatac cgttcgggaa atggggggtaa caactgctgg gcgtatcgat      420
ggtcgctcag gcgtgtgggt gccatcgact accgctgcga aagacccggc agcatcgcac      480
cgagaccgca agattgcggc cttaggcatc cgcattacgc gtggggttac catgcatggt      540
ctggcgctca attgcgacaa tatcttggac tactacgagc acattattgc ctgcggtatt      600
gatgatgccg atatcaccac cctggcgcta gagctgggcc gcgacgtcac cgtagatgat      660
gcggttgagc ccttgctcat tgcgcttgac gatgccttgg ccggccgcat ggtcgtcgcc      720
gaccacactt tcgcatctgc cccagacccc atcaaattag ctaatgagaa agcgcgccaa      780
gcacgcgcgc agtcttcctt gactgatcat gcaggctctt aa                         822
```

```
<210> SEQ ID NO 32
<211> LENGTH: 43
<212> TYPE: DNA
<213> ORGANISM: Artificial Sequence
<220> FEATURE:
<223> OTHER INFORMATION: primer

<400> SEQUENCE: 32
gccgatcttt gcggggatac tagtcaggat gcaattgcca tcc                         43
```

```
<210> SEQ ID NO 33
<211> LENGTH: 34
<212> TYPE: DNA
<213> ORGANISM: Artificial Sequence
<220> FEATURE:
<223> OTHER INFORMATION: primer

<400> SEQUENCE: 33
atgcgccatt agcgtggttg caccggttgc tacc                                   34
```

```
<210> SEQ ID NO 34
<211> LENGTH: 34
<212> TYPE: DNA
<213> ORGANISM: Artificial Sequence
<220> FEATURE:
<223> OTHER INFORMATION: primer

<400> SEQUENCE: 34
tagcaaccgg tgcaaccacg ctaatggcgc attg                                   34
```

```
<210> SEQ ID NO 35
<211> LENGTH: 43
<212> TYPE: DNA
<213> ORGANISM: Artificial Sequence
<220> FEATURE:
<223> OTHER INFORMATION: primer

<400> SEQUENCE: 35
gggttgggtt ttcccgatct cgagcagcaa gcccatgccc aag                         43
```

```
<210> SEQ ID NO 36
```

<211> LENGTH: 41
<212> TYPE: DNA
<213> ORGANISM: Artificial Sequence
<220> FEATURE:
<223> OTHER INFORMATION: primer

<400> SEQUENCE: 36
tgggcatggg cttgctgctc gagagaaaca tcccagcgct a                          41

<210> SEQ ID NO 37
<211> LENGTH: 43
<212> TYPE: DNA
<213> ORGANISM: Artificial Sequence
<220> FEATURE:
<223> OTHER INFORMATION: primer

<400> SEQUENCE: 37
gggttgggtt ttcccgatct cgagcgattg cgtggcctcc aac                        43

<210> SEQ ID NO 38
<211> LENGTH: 952
<212> TYPE: PRT
<213> ORGANISM: Corynebacterium ammoniagenes

<400> SEQUENCE: 38

Met Asp Phe Ile Ala Arg His Leu Gly Pro Asp Ala Thr Glu Ser Lys
1               5                   10                  15

Asp Met Leu Ala Arg Val Gly Tyr Asp Ser Val Glu Ala Leu Val Thr
            20                  25                  30

Ser Ala Ile Pro Gln Ser Ile Ser Ile Thr Asp Ala Leu Asn Met Pro
        35                  40                  45

Gln Ala Leu Ser Glu Thr Asp Ala Gln Ala Lys Leu Arg Ala Tyr Ala
    50                  55                  60

Asp Lys Asn Val Val Leu Lys Ser Phe Tyr Gly Gln Gly Tyr Ser Asp
65                  70                  75                  80

Thr Ile Thr Pro Ala Val Ile Arg Arg Gly Leu Val Glu Asp Ala Gly
                85                  90                  95

Trp Tyr Thr Ala Tyr Thr Pro Tyr Gln Pro Glu Ile Ser Gln Gly Arg
            100                 105                 110

Leu Glu Ser Leu Leu Asn Phe Gln Thr Met Val Gln Asp Leu Thr Gly
        115                 120                 125

Leu Pro Ile Ala Asn Ala Ser Leu Leu Asp Glu Ala Ser Ala Val Ala
    130                 135                 140

Glu Ala Val Gly Leu Met Ser Arg Ala Val Lys Lys Gly Arg Arg Val
145                 150                 155                 160

Leu Leu Asp Ala Arg Leu His Pro Gln Val Leu Thr Val Ala Ala Glu
                165                 170                 175

Arg Ala Arg Ala Ile Asp Leu Glu Val Glu Ile Ala Asp Leu Ser Asn
            180                 185                 190

Gly Val Val Gly Glu Asp Leu Val Gly Ala Val Val Ala Tyr Thr Gly
        195                 200                 205

Thr Glu Gly Asp Ile Phe Asp Pro Arg Ala Val Ile Glu Glu Ile His
    210                 215                 220

Gly Arg Gly Gly Leu Val Ser Val Ala Ala Asp Leu Leu Ser Leu Leu
225                 230                 235                 240

Leu Leu Glu Gly Pro Gly Ser Phe Gly Ala Asp Ile Val Ile Gly Ser
                245                 250                 255

Ser Gln Arg Phe Gly Val Pro Leu Phe Phe Gly Gly Pro His Ala Ala

-continued

```
                 260                 265                 270

Phe Met Ala Val Thr Asp Lys Leu Lys Arg Gln Met Pro Gly Arg Leu
        275                 280                 285

Val Gly Val Ser Val Asp Ser Glu Gly Arg Pro Ala Tyr Arg Leu Ala
        290                 295                 300

Leu Gln Thr Arg Glu Gln His Ile Arg Arg Glu Arg Ala Thr Ser Asn
305                 310                 315                 320

Ile Cys Thr Ala Gln Ala Leu Leu Ala Asn Val Ala Ala Met Tyr Ala
                325                 330                 335

Val Tyr His Gly Pro Glu Gly Leu Lys Glu Ile Ala Asn His Val His
                340                 345                 350

Ser Leu Ala Ala Ser Phe Ala Gly Ala Val Thr Thr Gln Gly Leu Lys
                355                 360                 365

Ile Thr Ser Ser Glu Phe Phe Asp Thr Val Thr Val Ala Gly Val Asp
        370                 375                 380

Ala Ala Ser Ile Lys Phe Ser Leu Glu Lys Ala Gly Tyr Leu Val Arg
385                 390                 395                 400

Thr Ile Gly Glu Asp Lys Val Ser Val Ser Phe Gly Glu Ser Ala Thr
                405                 410                 415

Gln Gly Asp Val Thr Val Leu Ala Asp Ala Phe Gly Ala Ala Ala Val
                420                 425                 430

Asp Asn Ala Asp Phe Pro Leu Pro Glu Ala Leu Thr Arg Thr Thr Glu
        435                 440                 445

Val Leu Thr His Glu Ile Phe Asn Ser Ile His Ser Glu Thr Gln Met
        450                 455                 460

Met Arg Tyr Leu Arg Lys Leu Gly Asp Lys Asp Leu Ala Leu Asp Arg
465                 470                 475                 480

Thr Met Ile Pro Leu Gly Ser Cys Thr Met Lys Leu Asn Pro Thr Ala
                485                 490                 495

Ala Met Glu Pro Ile Thr Trp Pro Glu Phe Ala Asn Val His Pro Tyr
                500                 505                 510

Ser Pro Glu Tyr Ala Thr Gln Gly Trp Arg Glu Leu Ile Glu Glu Leu
        515                 520                 525

Glu Gly Trp Leu Ala Glu Leu Thr Gly Tyr Ala Lys Val Ser Ile Gln
        530                 535                 540

Pro Asn Ala Gly Ser Gln Gly Glu Leu Ala Gly Leu Leu Ala Ile Arg
545                 550                 555                 560

Arg Tyr His Val Ala Asn Gly Asp Thr Asn Arg Asp Ile Val Leu Ile
                565                 570                 575

Pro Ala Ser Ala His Gly Thr Asn Ala Ala Ser Ala Thr Leu Ala Asn
                580                 585                 590

Leu Arg Val Val Val Lys Thr Ala Glu Asp Gly Ser Ile Asp Leu
                595                 600                 605

Glu Asp Leu Asp Ala Lys Ile Ala Lys His Gly Gln Asn Met Ala Gly
        610                 615                 620

Ile Met Ile Thr Tyr Pro Ser Thr His Gly Val Phe Asp Pro Glu Val
625                 630                 635                 640

Arg Glu Val Cys Asp Lys Ile His Ala Ala Gly Gly Gln Val Tyr Ile
                645                 650                 655

Asp Gly Ala Asn Met Asn Ala Leu Thr Gly Trp Ala Gln Pro Gly Lys
                660                 665                 670

Phe Gly Gly Asp Val Ser His Leu Asn Leu His Lys Thr Phe Thr Ile
        675                 680                 685
```

```
Pro His Gly Gly Gly Gly Pro Gly Val Gly Pro Ile Gly Val Ala Glu
    690             695             700

His Leu Ile Pro Phe Leu Pro Thr Asp Ala Ala Ala Asp Glu Leu Asp
705             710             715             720

Pro Ala Asn Pro Thr Pro Val Glu Gln Gly Val Pro Ile Thr Ala Ser
            725             730             735

Gln Phe Gly Ser Ala Gly Val Leu Pro Ile Thr Trp Ala Tyr Ile Ala
            740             745             750

Met Thr Gly Gly Glu Gly Leu Thr Ser Ala Thr Ala His Ala Ile Leu
            755             760             765

Gly Ala Asn Tyr Leu Ala Arg Glu Leu Ser Asp Ser Phe Pro Ile Leu
    770             775             780

Phe Thr Gly Asn Glu Gly Leu Val Ala His Glu Cys Ile Leu Asp Leu
785             790             795             800

Arg Ala Leu Thr Asp Ala Ser Gly Val Thr Ala Ala Asp Val Ala Lys
            805             810             815

Arg Leu Ile Asp Phe Gly Phe His Ala Pro Thr Leu Ala Phe Pro Val
            820             825             830

Ala Gly Thr Leu Met Val Glu Pro Thr Glu Ser Glu Asp Ile Ala Glu
            835             840             845

Leu Asp Arg Phe Ile Glu Ala Met Arg Thr Ile Arg Ala Glu Ile Gln
    850             855             860

Glu Ile Ile Asp Gly Lys Ile Ala Tyr Glu Asp Ser Val Ile Arg His
865             870             875             880

Ala Pro Tyr Thr Ala Pro Ser Val Ser Ser Asp Asp Trp Glu Tyr Ser
            885             890             895

Phe Ser Arg Glu Lys Ala Ala Trp Pro Val Pro Ser Leu Arg Leu Asn
            900             905             910

Lys Tyr Phe Pro Pro Val Arg Arg Leu Asp Glu Ala Tyr Gly Asp Arg
            915             920             925

Asn Leu Val Cys Ser Cys Pro Pro Glu Ala Phe Asp Phe Asp Ala
    930             935             940

Asp Thr Asp Ser Thr Glu Glu Ala
945             950
```

```
<210> SEQ ID NO 39
<211> LENGTH: 367
<212> TYPE: PRT
<213> ORGANISM: Corynebacterium ammoniagenes

<400> SEQUENCE: 39
```

```
Met Ser Glu Leu Arg Gln Ser Pro Leu His Ala Glu His Glu Lys Leu
1               5               10              15

Gly Ala Ser Phe Thr Ala Phe Gly Pro Trp Asn Met Pro Leu Lys Tyr
            20              25              30

Gly Lys Glu Leu Asp Glu His His Ala Val Arg Asn Ala Val Gly Met
        35              40              45

Phe Asp Leu Ser His Met Gly Glu Ile Trp Val Asn Gly Pro Asp Ala
    50              55              60

Ala Ala Phe Leu Ser Tyr Ala Leu Ile Ser Asn Met Glu Thr Val Lys
65              70              75              80

Asn Gly Lys Ala Lys Tyr Ser Met Ile Val Ala Glu Asp Gly Gly Ile
            85              90              95

Ile Asp Asp Leu Ile Ser Tyr Arg Phe Ser Asp Thr Lys Phe Leu Val
```

-continued

```
              100              105              110
Val Pro Asn Ala Gly Asn Thr Asp Val Val Trp Glu Ala Phe Asn Gln
        115              120              125

Arg Ile Glu Gly Phe Asp Val Glu Leu Asn Asn Glu Ser Leu Asp Val
    130              135              140

Ala Met Ile Ala Leu Gln Gly Pro Asn Ala Ala Lys Val Leu Val Glu
145              150              155              160

Gln Val Ala Glu Glu Ser Lys Glu Glu Val Glu Asn Leu Pro Tyr Tyr
                165              170              175

Ala Ala Thr Met Ala Lys Val Ala Asp Val Asp Thr Ile Val Ala Arg
            180              185              190

Thr Gly Tyr Thr Gly Glu Asp Gly Phe Glu Leu Met Ile Tyr Asn Ala
        195              200              205

Asp Ala Thr Lys Leu Trp Gln Leu Phe Ile Asp Gln Asp Gly Val Thr
    210              215              220

Pro Cys Gly Leu Ala Ser Arg Asp Ser Leu Arg Leu Glu Ala Gly Met
225              230              235              240

Pro Leu Tyr Gly Asn Glu Leu Ser Arg Asp Ile Thr Pro Val Glu Ala
                245              250              255

Gly Met Gly Val Ala Phe Lys Lys Thr Ala Asp Phe Val Gly Ala
            260              265              270

Glu Val Leu Arg Gln Arg Leu Glu Glu Gly Pro Lys Gln Val Ile Lys
        275              280              285

Ala Leu Thr Ser Ser Glu Arg Arg Ala Ala Arg Thr Gly Ala Glu Ile
    290              295              300

Tyr Ala Gly Glu Gln Leu Val Gly Thr Val Thr Ser Gly Gln Pro Ser
305              310              315              320

Pro Thr Leu Gly His Pro Ile Ala Leu Ala Leu Val Asp Thr Ala Ala
                325              330              335

Asn Leu Glu Glu Gly Ala Glu Val Glu Val Asp Ile Arg Gly Lys Arg
            340              345              350

Tyr Pro Phe Thr Val Thr Lys Thr Pro Phe Tyr Ser Arg Glu Lys
        355              360              365
```

```
<210> SEQ ID NO 40
<211> LENGTH: 129
<212> TYPE: PRT
<213> ORGANISM: Corynebacterium ammoniagenes

<400> SEQUENCE: 40

Met Ala Asn Leu Pro Ala Glu Phe Thr Tyr Ser Glu Asp His Glu Trp
1               5               10              15

Ile Asn Ala Ala Gln Asp Ala Ile Val Gly Lys Thr Val Arg Ile Gly
            20              25              30

Ile Thr Ser Val Ala Ala Asp Arg Leu Gly Glu Val Val Phe Ala Glu
        35              40              45

Leu Pro Ala Val Gly Asp Ser Val Thr Ala Gly Glu Thr Cys Gly Glu
    50              55              60

Val Glu Ser Thr Lys Ser Val Ser Asp Leu Tyr Ser Pro Val Thr Gly
65              70              75              80

Thr Val Thr Ala Val Asn Glu Thr Val His Asp Asp Tyr Glu Ile Ile
                85              90              95

Asn Asn Asp Pro Phe Gly Glu Gly Trp Leu Phe Glu Val Glu Val Glu
            100             105             110
```

```
Glu Leu Gly Glu Val Met Thr Ala Asp Glu Tyr Ala Ala Glu Asn Gly
        115                 120                 125

Ile

<210> SEQ ID NO 41
<211> LENGTH: 353
<212> TYPE: PRT
<213> ORGANISM: Corynebacterium ammoniagenes

<400> SEQUENCE: 41

Met Leu Arg Ile Glu Lys Lys Asn Ala Glu Ser Pro Ile Glu Gln Lys
1               5                   10                  15

Pro Arg Trp Ile Arg Asn Gln Val Arg Thr Gly Pro Gly Tyr Glu Asp
            20                  25                  30

Met Lys Lys Arg Val Ala Gly Ala Gly Leu His Thr Val Cys Gln Glu
        35                  40                  45

Ala Gly Cys Pro Asn Ile His Glu Cys Trp Glu Ser Arg Glu Ala Thr
    50                  55                  60

Phe Leu Ile Gly Gly Asp Arg Cys Thr Arg Arg Cys Asp Phe Cys Asp
65                  70                  75                  80

Ile Ala Thr Gly Lys Pro Gln Ala Leu Asp Thr Asp Glu Pro Arg Arg
                85                  90                  95

Val Ser Glu Asn Ile Gln Glu Met Asn Leu Asn Tyr Ala Thr Ile Thr
            100                 105                 110

Gly Val Thr Arg Asp Asp Leu Pro Asp Glu Gly Ala Trp Leu Tyr Ala
        115                 120                 125

Glu Val Val Arg Lys Ile His Glu Lys Asn Pro His Thr Gly Val Glu
        130                 135                 140

Asn Leu Thr Pro Asp Phe Ser Gly Lys Pro Asp Leu Leu Gln Glu Val
145                 150                 155                 160

Phe Glu Ala Arg Pro Glu Val Phe Ala His Asn Leu Glu Thr Val Pro
                165                 170                 175

Arg Ile Phe Lys Arg Ile Arg Pro Ala Phe Arg Tyr Glu Arg Ser Leu
            180                 185                 190

Asp Val Leu Gln Gln Ala His Asp Phe Gly Leu Ile Thr Lys Ser Asn
            195                 200                 205

Leu Ile Leu Gly Met Gly Glu Thr Glu Glu Glu Ile Gln Glu Ala Leu
        210                 215                 220

Arg Asp Met Arg Ser Val Gly Thr Asp Ile Ile Thr Ile Thr Gln Tyr
225                 230                 235                 240

Leu Arg Pro Gly Pro Arg Phe His Pro Ile Glu Arg Trp Val Arg Pro
                245                 250                 255

Glu Glu Phe Ile Ala His Ser Glu Tyr Ala Lys Glu Leu Gly Phe Thr
            260                 265                 270

Val Met Ser Gly Pro Leu Val Arg Ser Ser Tyr Arg Ala Gly Lys Leu
        275                 280                 285

Tyr Thr Gln Ala Met Lys Ala Arg Gly Trp Glu Leu Pro Glu Asn Leu
    290                 295                 300

Lys His Leu Glu Glu Thr Ser Asp Gly Ala Thr Ala Gln Glu Ala Ser
305                 310                 315                 320

Ser Leu Leu Lys Lys Tyr Gly Pro Ser Glu Glu Thr Pro Val Thr Ser
                325                 330                 335

Arg Met Ala Lys Thr Pro Val Gly Ala Asp Lys Phe Thr Ala Ser Ile
            340                 345                 350
```

-continued

```
Arg

<210> SEQ ID NO 42
<211> LENGTH: 273
<212> TYPE: PRT
<213> ORGANISM: Corynebacterium ammoniagenes

<400> SEQUENCE: 42

Met Thr Ala Pro Arg Asp Pro Phe Phe Pro Ala Asp Arg Ser Ile Arg
1               5                   10                  15

Ala Ser Thr Ala Pro Val Glu Val Arg Arg Leu Gly Arg Met Asp Tyr
                20                  25                  30

Gln Glu Ala Trp Asp Tyr Gln Ala Glu Val Ala Ala Gln Arg Ala Arg
            35                  40                  45

Asp Glu Val Ala Asp Thr Leu Leu Val Val Glu His Pro Ala Val Tyr
        50                  55                  60

Thr Ala Gly Lys Arg Thr Gln Pro Glu Asp Met Pro Thr Asn Gly Leu
65                  70                  75                  80

Pro Val Ile Asn Val Asp Arg Gly Gly Arg Ile Thr Trp His Gly Glu
                85                  90                  95

Gly Gln Leu Val Val Tyr Pro Ile Ile Lys Leu Ala Glu Pro Val Asp
            100                 105                 110

Val Val Asp Tyr Val Arg Arg Leu Glu Glu Ala Val Ile His Thr Val
            115                 120                 125

Arg Glu Met Gly Val Thr Thr Ala Gly Arg Ile Asp Gly Arg Ser Gly
        130                 135                 140

Val Trp Val Pro Ser Thr Thr Ala Ala Lys Asp Pro Ala Ala Ser His
145                 150                 155                 160

Arg Asp Arg Lys Ile Ala Ala Leu Gly Ile Arg Ile Thr Arg Gly Val
                165                 170                 175

Thr Met His Gly Leu Ala Leu Asn Cys Asp Asn Ile Leu Asp Tyr Tyr
                180                 185                 190

Glu His Ile Ile Ala Cys Gly Ile Asp Asp Ala Asp Ile Thr Thr Leu
            195                 200                 205

Ala Leu Glu Leu Gly Arg Asp Val Thr Val Asp Asp Ala Val Glu Pro
        210                 215                 220

Leu Leu Ile Ala Leu Asp Asp Ala Leu Ala Gly Arg Met Val Val Ala
225                 230                 235                 240

Asp His Thr Phe Ala Ser Ala Pro Asp Pro Ile Lys Leu Ala Asn Glu
                245                 250                 255

Lys Ala Arg Gln Ala Arg Ala Gln Ser Ser Leu Thr Asp His Ala Gly
            260                 265                 270

Ser
```

MICROORGANISM HAVING ENHANCED L-THREONINE PRODUCING ABILITY AND METHOD FOR PRODUCING THREONINE USING THE SAME

CROSS-REFERENCE TO RELATED APPLICATIONS

The present application is a 35 USC 371 national phase filing of PCT/KR2020/003318 filed on Mar. 10, 2020, which claims the benefit of and priority to Korean Patent Application No. 10-2019-0046935 filed on Apr. 22, 2019, both applications are incorporated herein by reference in their entirety.

INCORPORATION BY REFERENCE

This application includes an electronically submitted Sequence Listing which has been submitted in ASCII format via EFS-Web and is hereby incorporated by reference in its entirety. The ASCII copy having been modified on Sep. 7, 2021, is named "059520 00024 ST25.txt" and is 53,909 bytes in size.

TECHNICAL FIELD

The present application relates to a microorganism having an enhanced L-threonine producing ability and a method for producing threonine using the same.

BACKGROUND ART

Threonine, an essential amino acid, is widely used in feeds, food additives, and animal growth promoters, and is also used in rehydration solutions for medical uses and synthetic materials for pharmaceutical uses. With regard to a method for producing threonine using a microorganism, methods for enhancing threonine biosynthesis genes (e.g., ppc, aspC, and thrABC) and for blocking a threonine degradation pathway are known for increasing the yield (Kwang-Ho Lee, et al., *Molecular System Biology* 2007). The genes involved in the threonine degradation pathway include tdh, tdcB, glyA, ilvA, etc., and among these, threonine deaminase (ilvA) is known to be the most important gene for threonine degradation. The deletion of ilvA among the degradation genes greatly improves the yield of threonine, but is problematic in that an expensive isoleucine auxotroph appears; therefore, applying attenuation of the ilvA activity and high-susceptibility mutation for isoleucine is generally known (Akhverdian Valery Z. et al.).

Meanwhile, with respect to the relationship between threonine and glycine, the main precursor of serine hydroxymethyltransferase, involved in glycine synthesis, is serine, and it is known that the enzymatic activity is 24 times higher when serine is used as a precursor than when threonine is used (Simic et al., *Appl Environ Microbiol.* 2002). However, the glycine uptake and threonine producing ability are not known.

DISCLOSURE

Technical Problem

The present inventors introduced a glycine transporter cycA derived from *Corynebacterium ammoniagenes* in order to develop accessible microorganisms by introducing glycine released out of the cell, and as a result, they developed a strain that produces L-threonine in high yield.

Technical Solution

One object of the present application provides a microorganism of the genus *Corynebacterium* for producing L-threonine having an enhanced glycine transporter activity.

Another object of the present application provides a composition for producing L-threonine, including the microorganism of the present application.

Still another object of the present application provides a method for producing L-threonine, including culturing the microorganism of the present application.

Yet another object of the present application provides the use of a microorganism of the genus *Corynebacterium* having an enhanced glycine transporter activity for the production of L-threonine.

Advantageous Effects

The microorganism for producing L-threonine of the present application has an excellent threonine producing ability and thus can be effectively applied to mass production of L-threonine.

DETAILED DESCRIPTION OF PREFERRED EMBODIMENTS

Hereinbelow, the present application will be described in detail. Meanwhile, each of the explanations and exemplary embodiments disclosed herein can be applied to other explanations and exemplary embodiments. That is, all combinations of various factors disclosed herein belong to the scope of the present application. Furthermore, the scope of the present application should not be limited by the specific disclosure provided hereinbelow.

Additionally, those of ordinary skill in the art may be able to recognize or confirm, using only conventional experimentation, many equivalents to the particular aspects of the present application described herein. Furthermore, it is also intended that these equivalents be included in the present application.

One aspect of the present application provides a microorganism of the genus *Corynebacterium* for producing L-threonine having an enhanced glycine transporter activity.

As used herein, the term "glycine transporter" may include any protein capable of introducing glycine into a cell, and it may specifically be D-serine/D-alanine/glycine transporter. The glycine transporter may be interchangeably used with D-serine/D-alanine/glycine transporter or a protein for glycine uptake.

The "D-serine/D-alanine/glycine transporter" is a protein that can be involved in the transport of all of serine, alanine, and glycine, and information thereof can be obtained by searching for the D-serine/D-alanine/glycine transporter sequence in a known database such as NCBI Genbank. The transporter may specifically be CycA or AapA, and more specifically a CycA protein, but is not limited thereto.

As used herein, the term "CycA protein" refers to a protein involved in serine, alanine, and glycine uptake. The CycA protein is encoded by the cycA gene, and the cycA gene is known to exist in microorganisms such as *Escherichia coli, Klebsiella pneumoniae, Mycobacterium bovis, Salmonella enterica, Erwinia amylovora*, and *Corynebacterium ammoniagenes*.

For the purpose of the present application, the CycA protein of the present application may include any protein as long as it can enhance the threonine producing ability. Specifically, the CycA protein may be derived from a microorganism of the genus *Corynebacterium*, and more specifically derived from *Corynebacterium ammoniagenes*, but is not limited thereto. *Corynebacterium ammoniagenes* is the same species as *Brevibacterium ammoniagenes*, and has been classified in the same taxon as *Corynebacterium stationis* and *Brevibacterium stationis* (*International Journal of Systematic and Evolutionary Microbiology* 60:874-879). Additionally, *Brevibacterium ammoniagenes* has been renamed as *Corynebacterium stationis*.

Accordingly, as used herein, the terms *Corynebacterium ammoniagenes, Brevibacterium ammoniagenes, Corynebacterium stationis*, and *Brevibacterium stationis* can be used interchangeably.

The CycA protein of the present application may include an amino acid sequence of SEQ ID NO: 16 or an amino acid sequence having at least 70% homology or identity thereto.

Specifically, the CycA protein may include an amino acid sequence of SEQ ID NO: 16 or an amino acid sequence having at least 70%, 75%, 80%, 85%, 86%, 87%, 88%, 89%, 90%, 91%, 92%, 93%, 94%, 95%, 96%, 97%, 98%, or 99% homology or identity to the amino acid sequence of SEQ ID NO: 16. Additionally, it is apparent that any amino add sequence, in which part of the sequence is deleted, modified, substituted, or added, may also fail within the scope of the present application as long as the amino add sequence has such a homology or identity and exhibits an effect corresponding to that of the above protein.

Further, a probe that may be prepared from a known gene sequence, for example, any polypeptide encoded by a polynucleotide which can hybridize with a sequence complementary to all or part of the nucleotide sequence under stringent conditions to encode the polypeptide, may include polypeptides having the activity of serine, alanine, and glycine uptake.

That is, as used herein, although it is described as "a protein or polypeptide including an amino acid sequence described by a specific sequence number", "a protein or polypeptide consisting of an amino acid sequence described by a specific sequence number', or a 'protein or polypeptide having an amino acid sequence described by a specific sequence number, it is apparent that any protein having an amino acid sequence in which part of the sequence is deleted, modified, substituted, conservatively substituted, or added can be used in the present application even if it has the same or corresponding activity as the polypeptide consisting of the amino acid sequence of the corresponding sequence number. For example, it may be a case where the N-terminus and/or C-terminus of the amino acid sequence is added with a sequence that does not alter the function of the protein, a naturally occurring mutation, a potential mutation thereof, a silent mutation, or a conservative substitution.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan.

As used herein, the term "polynucleotide" has a meaning which collectively includes DNA or RNA molecules. Nucleotides, which are the basic structural units of the polynucleotides, include not only natural nucleotides but also modified analogs thereof in which sugar or base sites are modified (see Scheit, *Nucleotide Analogs*, John Wiley, New York (1980); Uhlman and Peyman, *Chemical Reviews*, 90:543-584 (1990)).

The polynucleotide may be a polynucleotide encoding the CycA protein of the present application, or may be a polynucleotide encoding a polypeptide having at least 70%, 75%, 80%, 85%, 86%, 87%, 88%, 89%, 90%, 91%, 92%, 93%, 94%, 95%, 96%, 97%, 98%, or 99% homology or identity to the CycA protein of the present application. Specifically, for example, the polynucleotide encoding the protein including the amino acid sequence of SEQ ID NO: 16 or the amino acid sequence having at least 70% homology or identity to SEQ ID NO: 16 may be a polynucleotide including an amino acid sequence of SEQ ID NO: 17 or having at least 70%, 75%, 80%, 85%, 86%, 87%, 88%, 89%, 90%, 91%, 92%, 93%, 94%, 95%, 96%, 97%, 98%, or 99% homology or identity to the polynucleotide sequence of SEQ ID NO: 17.

Further, it is apparent that due to codon degeneracy, proteins including the amino acid sequence of SEQ ID NO: 16 or having at least 70% identity to SEQ ID NO: 16, or polynucleotides that can be translated into proteins having a homology or identity thereto may also be included. Additionally, the polynucleotide of the present application may include a probe that may be prepared from a known gene sequence, for example, any polynucleotide sequence which can hybridize with a sequence complementary to all or part of the polynucleotide sequence under stringent conditions to encode proteins including the amino acid sequence of SEQ ID NO: 16 or having at least 70% identity thereto, without limitation. The "stringent conditions" refer to conditions under which specific hybridization between polynucleotides is allowed. Such conditions are specifically described in the literature (see J. Sambrook et al., *Molecular Cloning, A Laboratory Manual*, 2nd Edition, Cold Spring Harbor Laboratory press, Cold Spring Harbor, New York, 1989; F. M. Ausubel et al., *Current Protocols in Molecular Biology*, John Wiley & Sons, Inc., New York). For example, the stringent conditions may include conditions under which genes having a high homology or identity of 70% or higher, 80% or higher, specifically 85% or higher, specifically 90% or higher, more specifically 95% or higher, much more specifically 97% or higher, and still much more specifically 99% or higher are hybridized with each other, and genes having a homology or identity lower than the above homologies or identities are not hybridized with each other, or washing conditions of Southern hybridization, that is, washing once, specifically twice or three times at a salt concentration and a temperature corresponding to 60° C., 1×SSC, 0.1% SDS, specifically 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenosine is complementary to thymine, and cytosine is complementary to guanine. Therefore, the polynucleotide of the present application may include isolated nucleotide fragments complementary to the entire sequence as well as polynucleotide sequences substantially similar thereto.

Specifically, the polynucleotides having a homology or identity may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

As used herein, the term "homology" or "identity" refers to a degree of relatedness between two given amino acid sequences or nucleotide sequences, and may be expressed as a percentage. The terms homology and identity may often be used interchangeably with each other. The sequence homology or identity of conserved polynucleotide or polypeptide sequences may be determined by standard alignment algorithms and can be used with a default gap penalty established by the program being used. Substantially, homologous or identical sequences are generally expected to hybridize to all or at least about 50%, 60%, 70%, 80%, or 90% of the entire length of the sequences under moderate or highly stringent conditions. Polynucleotides that contain degenerate codons instead of codons in hybridizing polynucleotides are also considered.

The homology or identity of the polypeptide or polynucleotide sequences may be determined by, for example, the BLAST algorithm according to the literature (see Karlin and Altschul, *Pro. Natl. Acad. Sci.* USA, 90, 5873 (1993)), or FASTA by Pearson (see *Methods Enzymol.,* 183, 63, 1990). Based on the algorithm BLAST, a program referred to as BLASTN or BLASTX has been developed (see http://www.ncbi.nlm.nih.gov). Further, whether any amino add or polynucleotide sequences have a homology, similarity, or identity with each other may be identified by comparing the sequences in a Southern hybridization experiment under stringent conditions as defined, and appropriate hybridization conditions defined are within the skill of the art, and may be determined by a method well known to those skilled in the art (for example, J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*).

As used herein, the term "enhancement of protein activity" means that the activity is enhanced as compared to the endogenous activity possessed by a microorganism or the activity before transformation. The enhancement of activity may include both introducing a foreign protein and enhancing the activity of an endogenous protein. That is, it includes introducing a foreign protein into a microorganism having an intrinsic activity of a specific protein, and introducing the protein into a microorganism having no intrinsic activity. The "introduction of the protein" means that the activity of a specific protein is introduced into a microorganism such that the protein activity is modified for expression. It can also be expressed as the enhancement of the activity of the corresponding protein.

As used herein, the term "endogenous" refers to a state originally possessed by a parent strain prior to transformation, when the traits of the microorganism are altered by way of genetic modification due to natural or artificial factors.

In the present application, the enhancement of activity may be performed by way of the following methods:

1) a method for increasing the copy number of the polynucleotide encoding the protein;

2) a method for modifying an expression regulatory sequence such that the expression of the polynucleotide is increased;

3) a method for modifying the polynucleotide sequence on a chromosome such that the activity of the protein is enhanced;

4) a method for introducing a foreign polynucleotide exhibiting the activity of the protein or a modified polynucleotide in which the codons of the above polynucleotide have been optimized; and 5) a method for modification to enhance the activity by way of a combination of the above methods, but the method is not limited thereto.

The increasing of the copy number of the polynucleotide in method 1) above may be performed in a form in which the polynucleotide is operably linked to a vector, or by inserting into a chromosome of a host cell, but is not particularly limited thereto. Specifically, it may be performed by operably linking the polynucleotide encoding the protein of the present application to a vector which can replicate and function regardless of the host cell, and introducing the same into the host cell. Alternatively, it may be performed by way of a method for increasing the copy number of the polynucleotide in the chromosome of the host cell by operably linking the polynucleotide to a vector which can insert the polynucleotide into the chromosome of the host cell, and introducing the same into the host cell.

Next, the modification of an expression regulatory sequence such that the expression of the polynucleotide is increased in method 2) may be performed by inducing a modification in the sequence through deletion, insertion, or non-conservative or conservative substitution of a nucleic acid sequence, or a combination thereof so as to further enhance the activity of the expression regulatory sequence, or by replacing with a nucleic acid sequence having a stronger activity, but is not particularly limited thereto. Additionally, the expression regulatory sequence may include a promoter, an operator sequence, a sequence encoding a ribosome binding domain, a sequence regulating the termination of transcription and translation, etc., but is not particularly limited thereto.

A strong heterologous promoter may be linked to the upstream region of the expression unit of the polynucleotide instead of the original promoter. Examples of the strong promoter include CJ7 promoter (Korean Patent No. 0620092 and International Publication No. WO 2006/065095), lysCP1 promoter (International Publication No. WO 2009/096689), EF-Tu promoter, groEL promoter, aceA or aceB promoter, etc., but the strong promoter is not limited thereto. Further, the modification of the polynucleotide sequence on a chromosome in method 3) may be performed by inducing a modification in the expression regulatory sequence through deletion, insertion, or non-conservative or conservative substitution of a nucleic acid sequence, or a combination thereof so as to further enhance the activity of the polynucleotide sequence, or by replacing the polynucleotide sequence with a polynucleotide sequence modified to have a stronger activity, but is not particularly limited thereto.

Additionally, the introduction a foreign polynucleotide sequence in method 4) may be performed by introducing into a host cell a foreign polynucleotide encoding a protein that exhibits an activity identical or similar to that of the protein above, or a modified polynucleotide in which the codons of the foreign polynucleotide have been optimized. The foreign polynucleotide may be used without limitation to its origin or sequence as long as it exhibits an activity identical or similar to that of the protein. Further, the foreign polynucleotide may be introduced into a host cell after optimization of its codons so as to achieve the optimized transcription and translation in the host cell. The introduction may be performed by those skilled in the art by selecting a suitable transformation method known in the art, and a protein can be produced as the introduced polynucleotides are expressed in the host cell, thereby increasing its activity.

Finally, the method for modification to enhance the activity by way of a combination of methods 1) to 4) in method 5) may be performed by way of a combined application of at least one of the following methods: increasing the copy number of the polynucleotide encoding the protein; modifying an expression regulatory sequence such that the expression of the polynucleotide is increased; modifying the polynucleotide sequence on a chromosome; and modifying a foreign polynucleotide exhibiting the activity of the protein or a codon-optimized modified polynucleotide thereof.

As used herein, the term "vector" refers to refers to a DNA construct containing the polynucleotide sequence encoding the target protein, which is operably linked to a suitable regulatory sequence such that the target protein can be expressed in an appropriate host. The regulatory sequence includes a promoter capable of initiating transcription, any operator sequence for the control of the transcription, a sequence encoding an appropriate mRNA ribosome binding domain, and a sequence regulating the termination of transcription and translation. After being transformed into a suitable host cell, the vector may be replicated or function irrespective of the host genome, and may be integrated into the host genome itself. For example, a polynucleotide encoding a target protein in the chromosome may be replaced with a modified polynucleotide through a vector for chromosomal insertion. The insertion of the polynucleotide into the chromosome may be performed by way of any method known in the art, for example, homologous recombination, but is not limited thereto.

The vector used in the present application is not particularly limited as long as it can be replicated in a host cell, and any vector known in the art may be used. Examples of conventionally used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used, and as a plasmid vector, those based on pBR, pUC, pBluescriptII, pGEM, pTZ, pCL, pET, etc. may be used. Specifically, the vectors pDZ, pACYC177, pACYC184, pCL, pECCG117, pUC19, pBR322, pMW118, pCC1BAC, etc. may be used.

As used herein, the term "transformation" refers to a process of introducing a vector including a polynucleotide encoding a target polypeptide into a host cell, thereby enabling expression of the polypeptide encoded by the polynucleotide in the host cell. As long as the transformed polynucleotide can be expressed in the host cell, it does not matter whether it is inserted into the chromosome of a host cell and located therein or located outside the chromosome, and both cases may be included. Additionally, the polynucleotide includes DNA and RNA which encode the target polypeptide. The polynucleotide may be introduced in any form as long as it can be introduced into a host cell and expressed therein. For example, the polynucleotide may be introduced into a host cell in the form of an expression cassette, which is a gene construct including all elements necessary for self-expression. The expression cassette may conventionally include a promoter operably linked to the polynucleotide, a terminator, a ribosome binding domain, and a stop codon. The expression cassette may be in the form of an expression vector capable of self-replication. Additionally, the polynucleotide may be introduced into a host cell as it is and operably linked to a sequence necessary for its expression in the host cell, but is not limited thereto.

Further, as used above, the term "operably linked" refers to a functional linkage between the above gene sequence and a promoter sequence which initiates and mediates the transcription of the polynucleotide encoding the target protein of the present application.

The method for transforming the vector of the present application includes any method of introducing a nucleic acid into a cell, and may be performed by selecting a suitable standard technique as known in the art depending on the host cell. For example, the transformation may be carried out via electroporation, calcium phosphate ($CaPO_4$) precipitation, calcium chloride ($CaCl_2$) precipitation, microinjection, a polyethylene glycol (PEG) technique, a DEAE—dextran technique, a cationic liposome technique, a lithium acetate—DMSO technique, etc., but the method is not limited thereto.

As used herein, the term "microorganism for producing L-threonine" includes all wild-type microorganisms, or naturally or artificially genetically modified microorganisms, and it may refer to a microorganism having an L-threonine producing ability, or a microorganism to which an L-threonine producing ability is imparted to a parent strain that does not have an L-threonine producing ability. Additionally, it may be a microorganism in which a particular mechanism is weakened or enhanced due to insertion of a foreign gene, or enhancement or inactivation of the activity of an endogenous gene, and it may be a microorganism in which genetic mutation occurs or activity is enhanced for the production of the desired L-threonine.

For example, the microorganism for producing L-threonine may be a microorganism having an enhanced glycine transporter activity. Additionally, it may be a microorganism in which feedback of an enzyme on the threonine biosynthesis pathway is inhibited, or may be a microorganism that produces threonine by enhancing or inhibiting an enzyme involved in the threonine biosynthesis pathway. Additionally, it may be a microorganism that produces threonine by inactivating the activity of an enzyme or protein that does not affect threonine biosynthesis, thereby facilitating the metabolism of the threonine biosynthesis pathway. Further, it may be a microorganism in which the activity of an intermediate, a cofactor, or a protein or enzyme on a pathway that consumes an energy source on the threonine biosynthesis pathway is inactivated.

More specifically, it may be a microorganism in which the feedback on the threonine biosynthesis pathway is inhibited by modifying the polypeptides of lysC (aspartate kinase) and hom (homoserine dehydrogenase), the protein expression involved in the increase of threonine production is enhanced, or the enzyme involved in threonine degradation pathway is inactivated.

However, this is merely an example, and the microorganism is not limited thereto. Additionally, it may be a microorganism that enhances the expression of genes encoding enzymes of various known L-threonine biosynthetic pathways or inactivates enzymes on degradation pathways. The microorganism for producing L-threonine can be prepared by applying various known methods.

As used herein, the term "inactivation of protein activity" means that a natural wild-type strain, a parent strain, or the corresponding protein have no expression of the enzyme or protein, or have no activity or decreased activity even though expressed, as compared to a non-modified strain. In particular, the decrease is a comprehensive concept including the case where the protein activity itself is decreased compared to the activity of the protein originally possessed by a microorganism due to the mutation of the gene encoding the protein, modification of the expression regulatory sequence, or deletion in a part or all of genes, etc.; the case where the overall level of intracellular protein activity is decreased compared to that of a natural strain or a strain before modification due to the inhibition of expression of the gene encoding the protein or the inhibition of translation; and a combination thereof. In the present application, the inactivation may be achieved by applying various methods well known in the art. Examples of the methods may include 1) a method for deleting a part or all of the gene encoding the protein; 2) a method for modifying the expression regulatory sequence such that the expression of the gene is decreased; 3) a method for modifying the gene sequence encoding the protein such that the protein activity is removed or weakened; 4) a method for introducing an antisense oligonucleotide (for example, antisense RNA) that binds complementarily to the transcript of the gene encoding the protein; 5) a method for adding a complementary sequence to the Shine-Dalgarno sequence upstream of the Shine-Dalgarno sequence of the gene encoding the protein to form a secondary structure, thereby inhibiting the ribosomal attachment; and 6) a reverse transcription engineering (RTE) method for adding a promoter at the 3' terminus of an open reading frame (ORF) of the polynucleotide sequence of the gene encoding the protein so as to be reversely transcribed; and a combination thereof, but is not particularly limited thereto.

For the purpose of the present application, the microorganism of the present application may be any microorganism as long as it includes the glycine transporter and is capable of producing L-threonine.

In the present application, the term "microorganism capable of producing L-threonine" can be interchangeably used with "microorganism producing L-threonine", "microorganism having an L-threonine producing ability", and "microorganism for producing L-threonine".

The microorganism producing threonine of the present application may be one in which the activity of the glycine cleavage protein is further enhanced. The "microorganism producing threonine" and "enhancement of protein activity" are the same as described above.

As used herein, the term "glycine cleavage protein" is a protein that is directly or indirectly involved in the glycine cleavage pathway, and may be used to mean each protein consisting the glycine cleavage system (GCV) or the complex of the protein or the glycine cleavage system itself.

Specifically, the glycine cleavage protein may be any one or more selected from the group consisting of T-protein (GcvT), P-protein (GcvP), L-protein (GcvL), or H-protein (GcvH) that constitute the glycine cleavage system, and LipB or LipA, which are coenzymes of the glycine cleavage system, but is not limited thereto (John E. Cronan, *Microbiology and Molecular Biology Reviews.*, 13 Apr. 2016). The glycine cleavage protein may be derived from a microorganism of the genus *Corynebacterium*, specifically *Corynebacterium ammoniagenes*, but is not limited thereto. The GcvP may include an amino acid sequence of SEQ ID NO: 38, GcvT may include an amino acid sequence of SEQ ID NO: 39, GcvH may include an amino acid sequence of SEQ ID NO: 40, LipA may include an amino acid sequence of SEQ ID NO: 41, and LipB may include an amino acid sequence of SEQ ID NO: 42 or an amino acid sequence having at least 70% homology to the respective amino acid sequence, but is not limited thereto. Specifically, the GcvP protein may include the amino acid sequence of SEQ ID NO: 38, or an amino acid sequence having at least 70%, 75%, 80%, 85%, 86%, 87%, 88%, 89%, 90%, 91%, 92%, 93%, 94%, 95%, 96%, 97%, 98%, or 99% homology or identity to the amino acid sequence of SEQ ID NO: 38. The description of homology or identity is the same for GcvT, GcvH, LipA, and LipB. Additionally, it is apparent that any protein having an amino acid sequence in which part of the amino add sequence is deleted, modified, substituted, or added may also fall within the scope of the present application as long as the amino add has such a homology or identity and exhibits an effect corresponding to that of the above protein.

Further, a probe that may be prepared from a known gene sequence, for example, any polypeptide having a glycine-degrading activity as a polypeptide encoded by a polynucleotide which can hybridize with a sequence complementary to all or part of the nucleotide sequence under stringent conditions to encode the polypeptide, may be included without limitation.

The homology or identity are as described above.

As used herein, the term "microorganism of the genus *Corynebacterium* for producing L-threonine" is a microorganism that produces L-threonine and may mean a microorganism belonging to the genus *Corynebacterium*. The microorganism producing L-threonine is the same as described above. Specifically, in the present application, the microorganism of the genus *Corynebacterium* having an L-threonine producing ability may mean a microorganism of the genus *Corynebacterium* in which the activity of the glycine transporter of the present application is enhanced, or which has been transformed with a vector containing the gene encoding the glycine transporter to have an improved L-threonine producing ability. Alternatively, it may mean a microorganism of the genus *Corynebacterium* in which the activity of the glycine cleavage protein is further enhanced, or which has been transformed with a vector containing the gene encoding the glycine cleavage protein to have an improved L-threonine producing ability. The "microorganism of the genus *Corynebacterium* having an improved L-threonine producing ability" may mean a microorganism in which the L-threonine producing ability is improved compared to a parent strain before transformation or a non-modified microorganism. The "non-modified microorganism" may refer to a natural strain of the genus *Corynebacterium* itself, a microorganism not containing the gene encoding the glycine transporter, or a microorganism that has not been transformed with a vector containing the gene encoding the glycine transporter.

As used herein, the term "microorganism of the genus *Corynebacterium*" may include all microorganisms of the genus *Corynebacterium*. Specifically, it may be *Corynebacterium glutamicum*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium ammoniagenes*, *Corynebacterium pollutisoli*, *Corynebacterium imitans*, *Corynebacterium testudinoris*, or *Corynebacterium flavescens*, and more specifically *Corynebacterium glutamicum*.

Another aspect of the present application provides a composition for producing L-threonine, including the microorganism for producing L-threonine of the present application.

The composition for producing L-threonine may refer to a composition capable of producing L-threonine by the microorganism for producing L-threonine of the present application. The composition may include the microorganism for producing L-threonine, and may include an additional composition capable of producing threonine using the strain without limitation. The additional component capable of producing threonine may further include, for example, any suitable excipient commonly used in a composition for fermentation, or a component of a medium. Such excipients may be, for example, preservatives, wetting agents, dispersing agents, suspending agents, buffers, stabilizing agents, or isotonic agents, but are not limited thereto.

Still another aspect of the present application provides a method for producing L-threonine, including culturing the microorganism.

The medium and other culture conditions used for culturing the microorganism of the present application may be any medium used for conventional cultivation of microorganisms without any particular limitation. Specifically, the microorganism of the present application may be cultured under aerobic or anaerobic conditions in a conventional medium containing an appropriate carbon source, nitrogen source, phosphorus source, inorganic compound, amino acid, and/or vitamin, while adjusting temperature, pH, etc.

The carbon source may include carbohydrates, such as glucose, fructose, sucrose, maltose, etc.; alcohols, such as sugar alcohols, glycerol, etc.; fatty acids, such as palmitic acid, stearic acid, linoleic acid, etc.; organic acids, such as pyruvic acid, lactic acid, acetic acid, citric acid, etc.; amino acids, such as glutamic acid, methionine, lysine, etc., but is not limited thereto. Additionally, the carbon source may include natural organic nutrients such as starch hydrolysate, molasses, blackstrap molasses, rice bran, cassava, sugar cane molasses, corn steep liquor, etc., and carbohydrates such as sterilized pretreated molasses (i.e., molasses converted to reducing sugar) may be used. In addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compound may include sodium chloride, calcium chloride, iron chloride, magnesium sulfate, iron sulfate, manganese sulfate, calcium carbonate, etc.

Additionally, amino acids, vitamins, and/or appropriate precursors may be included. These media or precursors may be added to a medium in a batch culture or continuous manner, but these phosphorus sources are not limited thereto.

In the present disclosure, the pH of a culture medium may be adjusted during the cultivation of a microorganism by adding a compound such as ammonium hydroxide, potassium hydroxide, ammonia, phosphoric acid, sulfuric acid, etc. to the culture medium in an appropriate manner. Additionally, during the cultivation, an antifoaming agent such as a fatty acid polyglycol ester may be added to prevent foam generation. In addition, oxygen or oxygen-containing gas may be injected into the medium in order to maintain an aerobic state of the medium; or nitrogen, hydrogen, or carbon dioxide gas may be injected without the injection of gas in order to maintain an anaerobic or microaerobic state of the medium.

The temperature of the culture medium may be in a range from 25° C. to 40° C., and more specifically from 28° C. to 37° C., but is not limited thereto. The cultivation may be continued until the useful materials are obtained in desired amounts, and specifically for 10 to 100 hours, but is not limited thereto.

The method for producing L-threonine may include a step of recovering L-threonine from at least one material selected from the microorganism, the medium, the culture medium thereof, the supernatant of the culture medium, the extract of the culture medium, and the lysate of the microorganism after the culturing step.

In the recovery step, L-threonine, which is the target material, can be recovered from the culture solution using a suitable method known in the art according to the culture method, for example, a batch, continuous, or fed-batch culture method. For example, for the recovery of L-threonine, methods such as precipitation, centrifugation, filtration, chromatography, and crystallization may be used. For example, a supernatant obtained by removing the biomass by centrifuging the culture medium at low speed may be separated through ion-exchange chromatography, but is not limited thereto.

The recovery step may include a purification process.

Yet another aspect of the present application provides the use of a microorganism of the genus *Corynebacterium* having an enhanced glycine transporter activity for the production of L-threonine.

The "glycine transporter", "enhancement of activity", or "microorganism of the genus *Corynebacterium*" are as described above.

Mode for Carrying Out the Invention

Hereinafter, the present application will be described in detail by way of Examples and Experimental Examples. However, these Examples and Experimental Examples are provided for illustrative purposes only, and the scope of the present application is not intended to be limited to or by these Examples and Experimental Examples.

Example 1: Preparation of L-Threonine-Producing Strain Using Wild-Type Microorganism of Genus *Corynebacterium*

Example 1-1: Preparation of Microbial Strain of Genus *Corynebacterium* Having L-Threonine Producing Ability L-Threonine-producing strains were developed from the wild-type *Corynebacterium glutamicum* ATCC13032. Specifically, in order to resolve the feedback inhibition by aspartate kinase (lysC), which serves as an important enzyme that is acted upon first in the threonine biosynthesis pathway, a strain was prepared in which leucine, which is an amino acid at position 377 of lysC, was substituted with lysine (SEQ ID NO: 1). Based on the strain, a threonine-producing strain was prepared by substituting arginine, which is an amino acid at position 398 of hom, with glutamine so as to resolve the feedback inhibition of homoserine dehydrogenase (hom) (SEQ ID NO: 6), which is important in the threonine biosynthesis pathway.

Example 1-1-1: Introduction of lysC Mutation

Specifically, in order to prepare strains in which the lysC (L377K) mutation was introduced, PCR was carried out based on the chromosome of ATCC13032 as a template using the primers of SEQ ID NOS: 2 and 3 or SEQ ID NOS: 4 and 5. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 1 minute. As a result, a DNA fragment (515 bp) in the 5' upstream region and a DNA fragment (538 bp) in the 3' downstream region were each obtained around the mutation of the lysC gene. PCR was carried out with the two amplified DNA fragments as a template using the primers of SEQ ID NO: 2 and SEQ ID NO: 5. PCR was carried out as follows: denaturation at 95° C. for 5 minutes; 28 cycles of denaturation at 95° C. for 30 seconds, annealing at 55° C. for 30 seconds, and polymerization at 72° C. for 2 minutes; and polymerization at 72° C. for 5 minutes. As a result, the DNA fragment (1023 bp) including the mutation of lysC gene, which encodes an aspartokinase variant in which leucine at position 377 was substituted with lysine, was amplified. The amplified product was purified using a PCR purification kit (QIAGEN) and used as an insert DNA fragment for the preparation of a vector. Meanwhile, after treating with restriction enzyme Smal, the ratio of the molar concentration (M) of the pDZ vector (KR Patent No. 10-0924065) heat-treated at 65° C. for 20 minutes to the insert DNA fragment amplified by the PCR above was set to be 1:2, and the vector was cloned using an Infusion Cloning Kit (TaKaRa) according to the manufacturer's manual, and thereby a pDZ-L377K vector for introducing the lysC(L377K) mutation into the chromosome was prepared.

The thus-prepared pDZ-L377K vector was transformed into the ATCC13032 by electroporation and subjected to secondary crossover, and thereby a strain in which each of the nucleotide modifications was substituted with modified nucleotides was obtained. The strain was named CJP1.

Example 1-1-2: Introduction of Hom Mutation

In order to prepare strains in which the hom(R398Q) mutation was introduced based on the CJP1 strain, PCR was carried out based on the chromosome of ATCC13032 as a template using the primers of SEQ ID NOS: 7 and 8 or SEQ ID NOS: 9 and 10. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 1 minute. As a result, a DNA fragment (668 bp) in the 5' upstream region and a DNA fragment (659 bp) in the 3' downstream region were each obtained around the mutation of the hom gene. PCR was carried out with the two amplified DNA fragments as a template and the primers of SEQ ID NO: 7 and SEQ ID NO: 10. PCR was carried out as follows: denaturation at 95° C. for 5 minutes; 28 cycles of denaturation at 95° C. for 30 seconds, annealing at 55° C. for 30 seconds, and polymerization at 72° C. for 2 minutes; and polymerization at 72° C. for 5 minutes. As a result, the DNA fragment (1327 bp)

including the mutation of hom gene, which encodes a homoserine dehydrogenase variant in which arginine at position 398 is substituted with glutamine, was amplified. The amplified product was purified using a PCR purification kit (QIAGEN) and used as an insert DNA fragment for the preparation of a vector. Meanwhile, after treating with restriction enzyme Smal, the ratio of the molar concentration (M) of the pDZ vector heat-treated at 65° C. for 20 minutes to the insert DNA fragment amplified by the PCR above was set to be 1:2, and the vector was cloned using an Infusion Cloning Kit (TaKaRa) according to the manufacturer's manual, and thereby a pDZ-R398Q vector for introducing the hom(R398Q) mutation into the chromosome was prepared.

The thus-prepared pDZ-R398Q vector was transformed into the Corynebacterium glutamicum CJP1 by electroporation and subjected to secondary crossover, and thereby a strain in which each of the nucleotide modifications was substituted with modified nucleotides was obtained. The strain was named CJP1-R398Q and deposited at the Korean Culture Center of Microorganisms (KCCM), an International Depositary Authority, under the Budapest Treaty, and was assigned Accession No. KCCM12120P (Korea Patent No. 10-1947959).

Example 1-2: Preparation of L-Threonine-Producing Strain Introduced with D-Alanine/D-Serine/Glycine Transporter Gene An experiment was performed to insert the D-alanine/D-serine/glycine transporter gene into the microorganism prepared in Example 1-1 on the chromosome of Corynebacterium glutamicum.

Example 1-2-1: Preparation of Strain Introduced with Corynebacterium ammoniagenes-Derived Glycine Transporter (CycA(Cam))

In order to insert the cycA gene encoding the glycine transporter protein, the Ncgl2131 gene encoding the transposon was used as an insertion site (Korean Patent No. 10-1126041; the method disclosed in Journal of Biotechnology 104, 5-25 Jorn Kalinowski et al., 2003 was used) (SEQ ID NO: 11). In order to prepare a vector for transposon insertion, PCR was performed using the primers of SEQ ID NOS: 12 and 13 or SEQ ID NOS: 14 and 15 based on the chromosome of ATCC13032 as a template. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 2 minute; and polymerization at 72° C. for 5 minutes. As a result, a DNA fragment (2041 bp) in the 5' upstream region and a DNA fragment (2040 bp) in the 3' downstream region were each obtained from the Ncgl2131 gene. PCR was carried out with the two amplified DNA fragments as a template using the primers of SEQ ID NO: 12 and SEQ ID NO: 15. PCR was carried out as follows: denaturation at 95° C. for 5 minutes; 28 cycles of denaturation at 95° C. for 30 seconds, annealing at 55° C. for 30 seconds, and polymerization at 72° C. for 4 minutes; and polymerization at 72° C. for 5 minutes. As a result, a DNA fragment (4066 bp) including the recognition sites of two restriction enzymes, Spel and Xhol, was amplified around the center. The amplified product was purified using a PCR purification kit (QIAGEN) and used as an insert DNA fragment for the preparation of a vector. Meanwhile, after treating with restriction enzyme SmaI, the ratio of the molar concentration (M) of the pDZ vector heat-treated at 65° C. for 20 minutes to the insert DNA fragment amplified by the PCR above was set to be 1:2, and the vector was cloned using an Infusion Cloning Kit (TaKaRa) according to the manufacturer's manual, and thereby a pDZ-N2131 vector for insertion into the Ncgl2131 gene position was prepared.

The thus-prepared pDZ-N2131 vector was transformed into the KCCM12120P strain obtained in Example 1-1 above by electroporation and subjected to secondary crossover, and thereby a strain in which Ncgl2131 was deleted on the chromosome was obtained. The strain was named KCCM12120P-N2131.

Meanwhile, in order to obtain a gene fragment having a D-alanine/D-serine/glycine transporter activity, PCR was performed using the primers of SEQ ID NO: 18 and SEQ ID NO: 19 based on the chromosome of *Corynebacterium ammoniagenes* ATCC6872 as a template. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 90 seconds; and polymerization at 72° C. for 5 minutes. As a result, a cycA gene fragment (1595 bp) was obtained, and the amplified product was purified using a PCR purification kit (QIAGEN) and used as an insert DNA fragment for the preparation of a vector (SEQ ID NO: 17).

PCR was performed using p117-cj7-gfp including the cj7 promoter derived from a known microorganism of the genus *Corynebacterium* (Korean Patent No. 10-0620092) as a template. As used herein, the term "p117" represents pECCG117, which is an *E. coli—Corynebacterium* shuttle vector (*Biotechnology Letters* 13(10):721-726, 1991). PfuUltra™ high-fidelity DNA polymerase (Stratagene) was used as a polymerase for the PCR reaction, and PCR was carried out using the primers of SEQ ID NOS: 21 and 22. PCR conditions were as follows: 28 cycles of denaturation at 95° C. for 30 seconds, annealing at 55° C. for 30 seconds, and polymerization at 72° C. for 30 seconds; and polymerization at 72° C. for 3 minutes. The amplified PCR product was purified using a PCR purification kit (QIAGEN) to obtain a cj7 fragment (350 bp) (SEQ ID NO: 20).

Sewing PCR was performed using the cj7 fragment and cycA fragment prepared above as a template and using the primers of SEQ ID NOS: 21 and 19. PCR was carried out as follows: 28 cycles of denaturation at 95° C. for 30 seconds, annealing at 55° C. for 30 seconds, and polymerization at 72° C. for 2 minutes; and polymerization at 72° C. for 5 minutes. As a result, a cj7-cycA gene fragment (1945 bp) was obtained, and the amplified product was purified using a PCR purification kit (QIAGEN) and used as an insert DNA fragment for the preparation of a vector. Meanwhile, after treating the thus-prepared pDZ-N2131 vector with restriction enzyme xhol, followed by heat treatment at 65° C. for 20 minutes, the ratio of the molar concentration (M) of the vector to the cj7-cycA fragment obtained above was set to be 1:2, and the vector was cloned using an Infusion Cloning Kit (TaKaRa) according to the manufacturer's manual, and thereby a pDZ-N2131/cj7-cycA(Cam) vector for inserting the cycA gene into the Ncgl2131 gene position was prepared.

The thus-prepared pDZ-N2131/cj7-cycA(Cam) vector was transformed into the KCCM12120P strain by electroporation and subjected to secondary crossover, and thereby a strain in which Ncgl2131 was substituted with cj7-cycA (Cam) on the chromosome was obtained. The strain was named KCCM12120P/cycA(Cam).

Example 1-2-2: Preparation of Strain Introduced with *E. coli*-Derived Glycine Transporter (CycA(Eco))

Meanwhile, in order to compare the *Corynebacterium ammoniagenes*-derived cycA gene and the activity thereof, a known cycA gene derived from *E. coli* K-12 was introduced into the KCCM12120P strain in the same manner as above (*Microbiology,* 141(Pt 1); 133-40, 1995). Specifically, PCR was performed using the primers of SEQ ID NOS: 25 and 26 based on the chromosome of *E. coli* K-12 W3110 as a template. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 1 minute; and polymerization at 72° C. for 5 minutes. As a result, a cycA gene fragment (1544 bp) was obtained, and the amplified product was purified using a PCR purification kit (QIAGEN) and used as an insert DNA fragment for the preparation of a vector (SEQ ID NO: 23).

Sewing PCR was performed using the cj7 fragment and cycA fragment prepared above as a template and using the primers of SEQ ID NOS: 21 and 26. PCR was carried out as follows: 28 cycles of denaturation at 95° C. for 30 seconds, annealing at 55° C. for 30 seconds, and polymerization at 72° C. for 90 seconds; and polymerization at 72° C. for 5 minutes. As a result, a cj7-cycA gene fragment (1894 bp) was obtained, and the amplified product was purified using a PCR purification kit (QIAGEN) and used as an insert DNA fragment for the preparation of a vector. Meanwhile, after treating the thus-prepared pDZ-N2131 vector with restriction enzyme xhol, followed by heat treatment at 65° C. for 20 minutes, the ratio of the molar concentration (M) of the vector to the cj7-cycA fragment obtained above was set to be 1:2, and the vector was cloned using an Infusion Cloning Kit (TaKaRa) according to the manufacturer's manual, and thereby a pDZ-N2131/cj7-cycA(Eco) vector for inserting the cycA gene into the Ncgl2131 gene position was prepared.

The thus-prepared pDZ-N2131/cj7-cycA(Eco) vector was transformed into the KCCM12120P strain by electroporation and subjected to secondary crossover, and thereby a strain in which Ncgl2131 was substituted with cj7-cycA (Eco) was obtained. The strain was named KCCM12120P/cycA(Eco).

Example 1-3: Evaluation of L-Threonine Producing Ability of Strains Introduced with CycA The L-threonine producing ability test was performed on the strains prepared in Example 1-2. Each strain obtained above was seeded into a 250 mL corner-baffle flask containing 25 mL of a seed medium and cultured at 30° C. for 20 hours at 200 rpm under shaking. Then, 1 mL of the seed culture solution was seeded into a 250 mL corner-baffle flask containing 24 mL of the L-threonine production medium below, and cultured at 30° C. for 48 hours at 200 rpm with shaking.

Seed Medium (pH 7.0)

Glucose 20 g, Peptone 10 g, Yeast Extract 5 g, Urea 1.5 g, $KH_2PO_4$ 4 g, $K_2HPO_4$ 8 g, $MgSO_4·7H_2O$ 0.5 g, Biotin 100 µg, Thiamine-HCl 1000 µg, Calcium-Pantothenic Acid 2000 µg, Nicotinamide 2000 µg (based on 1 L of distilled water)

L-Threonine Production Medium (pH 7.2)

Glucose 30 g, $KH_2PO_4$ 2 g, Urea 3 g, $(NH4)_2SO_4$ 40 g, Peptone 2.5 g, CSL (Sigma) 5 g (10 mL), $MgSO_4 \cdot 7H_2O$ 0.5 g, Leucine 400 mg, $CaCO_3$ 20 g (based on 1 L of distilled water)

After completion of the culture, the production amount of various amino acids produced was measured by HPLC. The results are shown in Table 1 below.

TABLE 1

| Strains | Amino acid (g/L) | | | | | | |
|---|---|---|---|---|---|---|---|
| | Thr | Gly | Ser | Lys | Ile | Ala | Val |
| KCCM12120P | 1.61 | 0.27 | 0.04 | 2.73 | 0.07 | 0.14 | 0.04 |
| KCCM12120P-N2131 | 1.60 | 0.28 | 0.04 | 2.74 | 0.08 | 0.15 | 0.05 |
| KCCM12120P/cycA(Cam) | 1.81 | 0.22 | 0.03 | 2.61 | 0.07 | 0.00 | 0.03 |
| KCCM12120P/cycA(Eco) | 1.37 | 0.30 | 0.05 | 2.92 | 0.07 | 0.02 | 0.03 |

As the production of L-threonine increases, the production of L-lysine decreases, and in contrast, as the production of L-threonine increase, L-isoleucine (Ile) and glycine (Gly), which can be by-products in the L-threonine biosynthesis pathway, can increase, and thus, their production was confirmed. Additionally, the production amount of serine (Ser), alanine (Ala), and valine (Val) was also confirmed in order to investigate their function as a transporter of the cycA gene.

As shown in Table 1 above, the KCCM12120P/cycA (Cam) strain introduced with the cycA gene derived from *Corynebacterium ammoniagenes* showed a 12.5% increase in L-threonine production and a 4% decrease in L-lysine production compared to the parent strain KCCM12120P. Additionally, due to the effect of introducing the cycA gene, it was confirmed that production of glycine was decreased by 18.5% compared to the parent strain, and the production of serine and valine were slightly decreased compared to the parent strain, and the production of alanine was significantly decreased and thus was not detected in the culture medium.

Meanwhile, it was confirmed that the KCCM12120P/cycA(Eco) strain introduced with *E. coli*-derived cycA gene showed a 14.9% decrease in L-threonine production and a 6.9% and 10% increase in L-lysine and glycine production compared to the parent strain, respectively. As such, the effects of introducing *E. coli*-derived cycA and *Corynebacterium ammoniagenes*-derived cycA genes were found to be significantly different, but in common, the concentration of alanine in the culture medium was significantly reduced. In addition, in the case of introducing *E. coli*-derived cycA or *Corynebacterium ammoniagenes*-derived cycA, there was no change in the production of isoleucine (Ile).

Based on the above results, it was confirmed that the introduction of the cycA gene derived from *Corynebacterium ammoniagenes* was effective in the production of L-threonine.

The KCCM12120P/cycA(Cam) was named CA09-0902 and deposited at the Korean Culture Center of Microorganisms, an International Depositary Authority, under the Budapest Treaty on Apr. 10, 2019, with Accession No. KCCM12484P.

Example 1-4: Preparation of L-Threonine-Producing Strains Introduced with Glycine Cleavage System—Related Genes Example 1-4-1: Preparation of Vector for Introduction of Glycine Cleavage Protein Since it had been previously confirmed that the activity of the glycine transporter had an effect on the increase in threonine producing ability, an experiment was carried out to confirm the threonine producing ability when the utilization of glycine introduced into the cell was further increased. Specifically, the glycine cleavage system (hereinafter, GCV system) was introduced. In the *Corynebacterium glutamicum* strain, only genes encoding L-proteins, LipB, and LipA, among the six proteins constituting the GCV system are known, but genes encoding the other three proteins are not known. Therefore, in order to introduce the GCV system derived from *Corynebacterium ammoniagenes*, vectors for introduction of gcvP (SEQ ID NO: 27), gcvT (SEQ ID NO: 28), gcvH (SEQ ID NO: 29), lipA (SEQ ID NO: 30), and lipB (SEQ ID NO: 31) were prepared. The following experiment was carried out. In order to obtain a gcvPT gene fragment among the glycine cleavage system (hereinafter, GCV system)-related genes, PCR was performed based on the chromosome of *Corynebacterium ammoniagenes* ATCC6872 as a template using primers of SEQ ID NOS: 32 and 33. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 5 minutes; and polymerization at 72° C. for 7 minutes. As a result, a gcvPT gene fragment (4936 bp) including a promoter was obtained, and the amplified product was purified using a PCR purification kit (QIAGEN) and used as an insert DNA fragment for the preparation of a vector (SEQ ID NOS: 27 and 28).

In order to obtain a gcvH-lipBA gene fragment, another GCV system-related gene, PCR was performed based on the chromosome of *Corynebacterium ammoniagenes* ATCC6872 as a template using primers of SEQ ID NOS: 34 and 35. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 3 minutes; and polymerization at 72° C. for 5 minutes. As a result, a gcvH-lipBA gene fragment (3321 bp) including a promoter was obtained, and the amplified product was purified using a PCR purification kit (QIAGEN) and used as an insert DNA fragment for the preparation of a vector (SEQ ID NOS: 29, 30, 31).

Sewing PCR was performed using the gcvPT fragment and gcvH-lipBA fragment obtained above as a template and using the primers of SEQ ID NOS: 32 and 35. PCR was carried out as follows: 28 cycles of denaturation at 95° C. for 30 seconds, annealing at 55° C. for 30 seconds, and polymerization at 72° C. for 10 minutes; and polymerization at 72° C. for 12 minutes. As a result, a gcvPTH-lipBA gene fragment (8257 bp) was obtained, and the amplified product was purified using a PCR purification kit (QIAGEN) and used as an insert DNA fragment for the preparation of a vector. Meanwhile, after treating the pDZ-N2131 vector prepared in Example 1-2 above with restriction enzymes spel and xhol, the ratio of the molar concentration (M) of the vector to the gcvPTH-lipBA fragment obtained above was set to be 1:2, and the vector was cloned using an Infusion Cloning Kit (TaKaRa) according to the manufacturer's manual, and thereby a pDZ-N2131/gcvPTH-lipBA vector for inserting the GCV system gene into the Ncgl2131 gene position was prepared.

Example 1-4-2: Preparation of Strains Introduced with Glycine Cleavage Protein PCR was performed based on the pDZ-N2131/cj7-cycA (Cam) vector obtained in Example 1-2 above as a template using primers of SEQ ID NOS: 36 and 37. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 90 seconds; and polymerization at 72° C. for 5 minutes. As a result, a cj7-cycA(Cam) gene fragment (1944 bp) was obtained, and the amplified product was purified using a PCR purification kit (QIAGEN) and used as an insert DNA fragment for the preparation of a vector. Meanwhile, after treating the pDZ-N2131/gcvPTH-lipBA vector prepared above with restriction enzyme xhol, followed by heat treatment at 65° C. for 20 minutes, the ratio of the molar concentration (M) of the vector to the cj7-cycA(Cam) fragment obtained above was set to be 1:2, and the vector was cloned using an Infusion Cloning Kit (TaKaRa) according to the manufacturer's manual, and thereby a pDZ-N2131/gcv-lip-cycA(Cam) vector for inserting the D-alanine/D-serine/glycine transporter gene and the GCV system gene into the Ncgl2131 gene position was prepared.

The thus-prepared pDZ-N2131/gcv-lip-cycA(Cam) vector was transformed into the KCCM12120P strain by electroporation and subjected to secondary crossover, and thereby a strain in which Ncgl2131 was substituted with gcvPTH-lipBA-cycA(Cam) was obtained. The strain was named KCCM12120P/gcv-lip-cycA(Cam).

Example 1-4-3: Evaluation of Threonine Producing Ability of Strains Introduced with Glycine Transporter and Glycine Cleavage Protein The L-threonine producing ability test was performed on the strains prepared in Examples 1-2 and 1-4-2. Each strain obtained above was seeded into a 250 mL corner-baffle flask containing 25 mL of the seed medium above and cultured at 30° C. for 20 hours at 200 rpm with shaking. Then, 1 mL of the seed culture solution was seeded into a 250 mL corner-baffle flask containing 24 mL of the L-threonine production medium above, and cultured at 30° C. for 48 hours at 200 rpm with shaking.

After completion of the culture, the production amount of various amino acids produced was measured by HPLC. The results are shown in Table 2 below.

TABLE 2

| Strains | Amino acid (g/L) | | | | | | |
|---|---|---|---|---|---|---|---|
| | Thr | Gly | Ser | Lys | Ile | Ala | Val |
| KCCM12120P | 1.61 | 0.27 | 0.04 | 2.73 | 0.07 | 0.14 | 0.04 |
| KCCM12120P-N2131 | 1.60 | 0.28 | 0.04 | 2.74 | 0.08 | 0.15 | 0.05 |
| KCCM12120P/cycA(Cam) | 1.81 | 0.22 | 0.03 | 2.34 | 0.07 | 0.00 | 0.03 |
| KCCM12120P/gcv-lip-cycA(Cam) | 2.04 | 0.13 | 0.02 | 2.36 | 0.10 | 0.00 | 0.01 |

As shown in Table 2, the KCCM12120P/gcv-lip-cycA (Cam) strain introduced with the D-alanine/D-serine/glycine transporter gene and the GCV system gene showed a 26.7% increase in L-threonine production compared to the parent strain KCCM12120P, which showed an improvement in the production by 12.7% compared to the KCCM12120P/cycA (Cam) strain in which only the cycA gene was introduced. Based on the result, it was confirmed that the L-threonine production of the strain introduced together with the GCV system gene was further increased compared to the that of the strain in which the cycA gene was introduced alone.

The L-lysine production of the KCCM12120P/gcv-lip-cycA(Cam) strain was decreased by 13.6% compared to KCCM12120P, and the L-lysine production of the KCCM12120P/cycA(Cam) strain was decreased by 14.3% compared to KCCM12120P. Additionally, the L-isoleucine production was increased in the KCCM12120P/gcv-lip-cycA(Cam) compared to that of KCCM12120P, but when considering the results of Examples 1-3, it can be found that the production of L-isoleucine, a by-product in the biosynthesis pathway, also increased due to the increase in L-threonine production.

The glycine production was decreased by 18.5% only when the cycA gene was introduced compared to the KCCM12120P strain, and decreased by 51.9% when the GCV system-related genes were introduced together compared to the KCCM12120P strain. The alanine production was significantly reduced only by introducing the cycA gene, and it was confirmed that there was no adverse effect due to the introduction of the GCV system. Although the production of serine and valine was significantly small, it was confirmed that both the KCCM12120P/cycA(Cam) strain and the KCCM12120P/gcv-lip-cycA(Cam) strain showed a decrease in the production of serine and valine compared to the parent strain KCCM12120P.

The KCCM12120P/gcv-lip-cycA(Cam) was named CA09-0905 and deposited at the Korean Culture Center of Microorganisms, an International Depositary Authority, under the Budapest Treaty on Apr. 10, 2019, with Accession No. KCCM12485P.

Based on the results above, it was confirmed that when the cycA gene, which is the D-alanine/D-serine/glycine transporter gene derived from *Corynebacterium ammoniagenes*, was introduced based on the L-threonine-producing strain of the genus *Corynebacterium*, the L-threonine production was increased. Additionally, it was confirmed that when the GCV system—related genes were introduced together with the cycA gene, the L-threonine production was significantly increased.

Example 2: Confirmation of L-Threonine Producing Ability of L-Threonine-Producing Strain KCCM11222P Introduced with cycA and Glycine Cleavage System As in Example 1, an experiment was performed to confirm the effect of introducing the cycA and GCV system into the existing threonine-producing strain.

Example 2-1: Introduction of cycA into L-Threonine-Producing Strain KCCM11222P The transformant vectors pDZ-N2131, pDZ-N2131/cj7-cycA(Cam) and pDZ-N2131/cj7-cycA(Eco) vectors used in Example 1 above were each transformed into *Corynebacterium glutamicum* KCCM11222P (Korean Patent No. 10-1335853), which is an L-threonine-producing strain, and subjected to secondary crossover, and thereby strains in which Ncgl2131 was deleted and substituted with cj7-cycA (Cam) or cj7-cycA(Eco) on the chromosome were each obtained. The strains were named KCCM11222P-N2131, KCCM11222P/cycA(Cam), or KCCM11222P/cycA(Eco), respectively.

The L-threonine producing ability test was performed on the thus-prepared strains. Each strain obtained above was seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 24 mL of the L-threonine production medium below, and cultured at 32° C. for 48 hours at 200 rpm with shaking.

Seed Medium (pH 7.0)

Glucose 20 g, Peptone 10 g, Yeast Extract 5 g, Urea 1.5 g, $KH_2PO_4$ 4 g, $K_2HPO_4$ 8 g, $MgSO_4 \cdot 7H_2O$ 0.5 g, Biotin 100 μg, Thiamine-HCl 1000 μg, Calcium-Pantothenic Acid 2000 μg, Nicotinamide 2000 μg (based on 1 L of distilled water)

L-Threonine Production Medium (pH 7.0)

Glucose 100 g, $KH_2PO_4$ 2 g, Urea 3 g, $(NH_4)_2SO_4$ 25 g, Peptone 2.5 g, CSL(Sigma) 5 g (10 mL), $MgSO_4 \cdot 7H_2O$ 0.5 g, Biotin 100 μg, Thiamine-HCl 1000 μg, Calcium-Pantothenic Acid 2000 μg, Nicotinamide 3000 μg, $CaCO_3$ 30 g (based on 1 L of distilled water)

After completion of the culture, the production amount of various amino acids produced was measured by HPLC. The results are shown in Table 3 below.

TABLE 3

| Strains | Amino acid (g/L) | | | | | | |
|---|---|---|---|---|---|---|---|
| | Thr | Gly | Ser | Lys | Ile | Ala | Val |
| KCCM11222P | 7.64 | 1.30 | 0.86 | 3.68 | 1.46 | 0.60 | 0.46 |
| KCCM11222P-N2131 | 7.66 | 1.28 | 0.88 | 3.68 | 1.47 | 0.59 | 0.41 |
| KCCM11222P/cycA(Cam) | 8.80 | 1.02 | 0.85 | 3.13 | 1.42 | 0.01 | 0.42 |
| KCCM11222P/cycA(Eco) | 6.67 | 1.35 | 0.90 | 4.42 | 1.49 | 0.05 | 0.40 |

As shown in Table 3, the KCCM11222P/cycA(Cam) showed a 15.2% increase in L-threonine production and a 14.9% decrease in L-lysine production compared to the parent strain KCCM11222P. Glycine and alanine production showed a decrease of 21.5% and 98.3%, respectively, compared to KCCM11222P, confirming that the results were similar to the evaluation results based on the KCCM12120P strain of Example 1. In the case of isoleucine, the KCCM11222P/cycA(Cam) strain showed a 3% decrease in isoleucine production compared to KCCM11222P, whereas the KCCM11222P/cycA(Eco) strain showed a 4% increase in isoleucine production compared to KCCM11222P, confirming that the introduction of cycA protein did not significantly affect the production of isoleucine. In particular, it was confirmed that the strain into which the *Corynebacterium ammoniagenes*-derived cycA gene was introduced showed a decrease in isoleucine production.

Meanwhile, the KCCM11222P/cycA(Eco) strain into which the *E. coli*-derived cycA gene was introduced showed a 12.7% decrease in L-threonine production and a 20.1% increase in L-lysine production compared to the KCCM11222P strain. Thus, it was confirmed that the *E. coli*-derived cycA gene had no effect on increasing L-threonine production.

Based on the results, it can be found that the introduction of the *Corynebacterium ammoniagenes*-derived cycA protein into a mutant strain having a threonine producing ability can increase the threonine producing ability.

Example 2-2: Introduction of cycA and GCV System into L-Threonine-Producing Strain KCCM11222P In the same manner as in Example 1, the pDZ-N2131/gcv-lip-cycA(Cam) vector prepared to confirm the combination effect of the cycA(Cam) gene and the GCV system gene was transformed into KCCM11222P strain and subjected to secondary crossover, and thereby a strain in which Ncgl2131 was substituted with gcvPTH-lipBA-cycA(Cam) was obtained. The strain was named KCCM11222P/gcv-lip-cycA(Cam).

The L-threonine producing ability test was performed on the thus-prepared strains. Each strain obtained above was seeded into a 250 mL corner-baffle flask containing 25 mL of the seed medium above and cultured at 30° C. for 20 hours at 200 rpm with shaking. Then, 1 mL of the seed culture solution was seeded into a 250 mL corner-baffle flask containing 24 mL of the L-threonine production medium, and cultured at 32° C. for 48 hours at 200 rpm with shaking.

After completion of the culture, the production amount of various amino acids produced was measured by HPLC. The results are shown in Table 4 below.

TABLE 4

| Strains | Amino acid (g/L) | | | | | | |
|---|---|---|---|---|---|---|---|
| | Thr | Gly | Ser | Lys | Ile | Ala | Val |
| KCCM11222P | 7.63 | 1.32 | 0.87 | 3.70 | 1.45 | 0.60 | 0.45 |
| KCCM11222P-N2131 | 7.64 | 1.29 | 0.88 | 3.68 | 1.45 | 0.58 | 0.40 |
| KCCM11222P/cycA(Cam) | 8.81 | 1.04 | 0.85 | 3.11 | 1.42 | 0.01 | 0.41 |
| KCCM11222P/gcv-lip-cycA(Cam) | 10.31 | 0.57 | 0.49 | 3.17 | 1.50 | 0.00 | 0.31 |

As shown in Table 4, the KCCM11222P/gcv-lip-cycA(Cam) strain showed a 35.1% increase in L-threonine production compared to the parent strain KCCM11222P, which was a 17.0% increase in L-threonine production compared to the KCCM11222P/cycA(Cam) strain introduced with the cycA gene alone. Based on the results, as in Example 1, it was confirmed that the L-threonine production of the strain introduced together with the GCV system gene was further increased compared to the strain introduced with the cycA gene alone even in the recombinant L-threonine-producing strain KCCM11222P.

The L-lysine production of the KCCM11222P/gcv-lip-cycA(Cam) strain was decreased by 14.3% compared to KCCM11222P, whereas the L-lysine production of the KCCM11222P/cycA(Cam) strain was decreased by 14.9% compared to KCCM11222P. The L-isoleucine production of the KCCM11222P/gcv-lip-cycA(Cam) was increased by 3.4% compared to KCCM11222P, and this can be interpreted as a secondary effect according to the increase in L-threonine production, considering the results of Example 2-1.

The glycine production was decreased by 21.1% when the cycA gene was introduced alone, and decreased by 56.8% when the GCV system genes were introduced together compared to the KCCM11222P strain. The alanine production was significantly decreased by the introduction of the cycA gene, and was further decreased by the introduction of the GCV system, and was not detected in the KCCM11222P/gcv-lip-cycA(Cam) strain. The production of serine and valine was decreased by 43.7% and 31.1%, respectively, in the KCCM11222P/gcv-lip-cycA(Cam) compared to the parent strain KCCM11222P.

Those of ordinary skill in the art will recognize that the present application may be embodied in other specific forms without departing from its spirit or essential characteristics. The described embodiments are to be considered in all respects only as illustrative and not restrictive. The scope of the present application is therefore indicated by the appended claims rather than by the foregoing description. All changes which come within the meaning and range of equivalency of the claims are to be embraced within the scope of the present application.

The invention claimed is:

1. An L-threonine producing *Corynebacterium glutamicum* microorganism having enhanced glycine transporter activity and increased production of L-threonine compared to a non-modified microorganism, wherein the microorganism comprises *Corynebacterium ammoniagenes* cycA gene encoding a CycA protein glycine transporter, wherein the CycA protein glycine transporter comprises the amino acid sequence of SEQ ID NO: 16.

2. The microorganism of claim 1, wherein the microorganism has enhanced glycine cleavage protein activity.

3. The microorganism of claim 2, wherein the glycine cleavage protein is at least one selected from the group consisting of GcvP, GcvT, GcvH, LipB, and LipA.

4. The microorganism of claim 3, wherein the glycine cleavage protein is derived from *Corynebacterium ammoniagenes*.

5. The microorganism of claim 3, wherein the GcvP comprises an amino acid sequence of SEQ ID NO: 38, GcvT comprises an amino acid sequence of SEQ ID NO: 39, GcvH comprises an amino acid sequence of SEQ ID NO: 40, LipA comprises an amino acid sequence of SEQ ID NO: 41, and LipB comprises an amino acid sequence of SEQ ID NO: 42, or an amino acid sequence having at least 90% sequence identity to the respective amino acid sequence.

6. A composition for producing L-threonine, comprising the L-threonine producing microorganism of claim 1.

7. A method for producing L-threonine, comprising:

culturing the L-threonine producing microorganism of claim 1; and recovering L-threonine from the microorganism or medium.

* * * * *